US006680335B2

(12) United States Patent
Tang

(10) Patent No.: US 6,680,335 B2
(45) Date of Patent: Jan. 20, 2004

(54) METHODS OF MODULATING PROTEIN TYROSINE KINASE FUNCTION WITH SUBSTITUTED INDOLINONE COMPOUNDS

(75) Inventor: Peng Cho Tang, Moraga, CA (US)

(73) Assignee: Sugen, Inc., South San Francisco, CA (US)

(*) Notice: Subject to any disclaimer, the term of this patent is extended or adjusted under 35 U.S.C. 154(b) by 60 days.

(21) Appl. No.: 10/013,944

(22) Filed: Dec. 13, 2001

(65) Prior Publication Data
US 2002/0183364 A1 Dec. 5, 2002

Related U.S. Application Data

(63) Continuation of application No. 09/407,164, filed on Sep. 28, 1999.
(60) Provisional application No. 60/102,178, filed on Sep. 28, 1998.

(51) Int. Cl.[7] ........................ A61K 31/404; C07D 403/06
(52) U.S. Cl. ........................................ 514/414; 548/455
(58) Field of Search ............................. 514/414; 548/455

(56) References Cited

U.S. PATENT DOCUMENTS

| 4,376,110 A | 3/1983 | David et al. |
| 4,966,849 A | 10/1990 | Vallee et al. |
| 5,217,999 A | 6/1993 | Levitzki et al. |
| 5,302,606 A | 4/1994 | Spada et al. |
| 5,330,992 A | 7/1994 | Eissenstat et al. |
| 5,339,992 A | 8/1994 | Barthomeuf et al. |
| 5,374,652 A | 12/1994 | Buzzetti et al. |
| 5,382,593 A | 1/1995 | Le Baut et al. |
| 5,409,949 A | 4/1995 | Buzzetti et al. |
| 5,650,415 A | 7/1997 | Tang et al. |

FOREIGN PATENT DOCUMENTS

| EP | 0 566 226 A1 | 10/1993 |
| WO | 91/15495 | 10/1991 |
| WO | 92/20642 | 11/1992 |
| WO | 92/21660 | 12/1992 |
| WO | 94/03427 | 2/1994 |
| WO | 94/10202 | 5/1994 |
| WO | 94/14808 | 7/1994 |
| WO | 96/22976 | 8/1996 |
| WO | WO 98/07695 | 2/1998 |
| WO | WO 98/076950 | 2/1998 |

OTHER PUBLICATIONS

Von Dobeneck Chem. Ber. (1969) 102 (4) 1347–56.*
Von Dobeneck, Chem. ber. 102 (4) 1347–56 1969.
Akbasak and Sunar–Akbasak et al., "Oncogenes: cause or consequence in the development of glial tumors," *J. Neurol. Sci.* 111:119–133 (1992).
Arteaga et al., "Blockade of the Type I Somatomedin Receptor Inhibits Growth of Human Breast Cancer Cells in Athymic Mice," *J. Clin. Invest.* 84:1418–1423 (1989).

Barbier et al., "Synthesis of isobrassilexin, a biologically active isomer of brassilexin a cruciferae phytoalexin," *Synthetic Communications* 23(22):3109–3117 (1993).
Baserga, "Oncogenes and the Strategy of Growth Factors," *Cell* 79:927–930 (1994).
Baserga, "The Insulin–like Growth Factor I Receptor: A Key to Tumor Growth?" *Cancer Research* 55:249–252 (1995).
Benzies et al., "2–formyl–3–methoxymethylindole, 3–ethoxymethyl–2–formyl–indole and 2–formyl–3–methylindole," *Synthetic Communications* 16(14):1799–1807 (1986).
Bolen et al., "The Src family of tyrosine protein kinases in hempoietic signal transduction," *FASEB J.* 6:3403–3409 (1992).
Chao, "Growth Factor Signaling: Where is the Specificity?" *Cell* 68:995–997 (1992).
Chatterjee et al., "Acylation of indoles by duff reaction and vilsmeier–haack formylation and conformation of N–formylindoles," *J. Org. Chem.* 88(23):4002–4004 (1973).
Coppola et al., "A Functional Insulin–Like Growth Factor I Receptor is Required for the Mitogenic and Transforming Activities of the Epidermal Growth Factor Receptor," *Molecular and Cellular Biology* 14:4588–4595 (1994).
De Vries et al., "The fms–Like Tyrosine Kinase, a Receptor for Vascular Endothelial Growth Factor," *Science* 255:989–991 (1992).
Dickson et al., "Tyrosine kinase receptor—nuclear protooncogene interactions in breast cancer," *Cancer Treatment Res.* 61:249–273 (1992).
Fantl et al., "Distinct Phosphotyrosines on a Growth Factor Receptor Bind to Specific Molecules That Mediate Different Signaling Pathways," *Cell* 69:413–423 (1992).
Fendly et al., "Characterization of Murine Monoclonal Antibodies Reactive to Either the Human Epidermal Growth Factor Receptor of HER2/neu Gene Product," *Cancer Research* 50:1550–1558 (1990).
Ferrara and Henzel, "Pituitary Follicular Cells Secrete a Novel Heparin–Binding Growth Factor Specific for Vascular Endothelial Cells," *Biochemical and Biophysical Research Communications* 161:851–858 (1989).
Fingl and Woodbury, "Chapter 1—General Principles," in *The Pharmacological Basis of Therapeutics* 5th edition, Goodman and Gilman editors, MacMillan Publishing Co., Inc., New York, pp. 1–46 (1975).
Floege et al., "Heparin suppresses mesangial cell proliferation and matrix expansion in experimental mesangioproliferative glomerulonephritis," *Kidney International* 43:369–380 (1993).

(List continued on next page.)

Primary Examiner—Robert Gerstl
(74) Attorney, Agent, or Firm—Beth A. Burrous; Foley & Lardner

(57) ABSTRACT

The invention relates to certain indolinone compounds, their method of synthesis, and a combinatorial library consisting of the indolinone compounds. The invention also relates to methods of modulating the function of protein kinases using indolinone compounds and methods of treating diseases by modulating the function of protein kinases and related signal transduction pathways.

13 Claims, No Drawings

OTHER PUBLICATIONS

Folkman and Shing, "Angiogenesi," *J. Biol. Chem.* 267:10931–10934 (1992).

Folkman, "Ch. 24. Angiogenesis," *Congress of Thrombosis and Haemostasis* (Verstraete et al., eds.) Leuven University Press, Leuven pp. 583–596 (1987).

Folkman, "What is the Evidence that Tumors are Angiogenesis Dependent?" *Journal of the National Cancer Institute* 82:4–6 (1990).

Gennaro (editor), *Remington's Pharmaceutical Sciences* (1990) (Table of Contents Only).

Goldring and Goldring, "Cytokines and Cell Growth Control," *Critical Reviews in Eukaryotic Gene Expression* 1:301–326 (1991).

Houck et al., "Dual Regulation of Vascular Endothelial Growth Factor Bioavailability by Genetic and Proteolytic Mechanisms," *J. Biol. Chem.* 267:26031–26037 (1992).

Jellinek et al., "Inhibition of Receptor Binding by High–Affinity RNA Ligands to Vascular Endothelial Growth Factor," *Biochemistry* 33:10450–10456 (1994).

Kendall and Thomas, "Inhibition of vascular endothelial cell growth factor activity by an endogenously encoded soluble receptor," *Proc. Natl. Acad. Sci. USA* 90:10705–10709 (1993).

Kim et al., "Inhibition of vascular endothelial growth factor–induced angiogenesis suppresses tumour growth in vivo," *Nature* 362:841–844 (1993).

Kinsella et al., "Protein Kinase C Regulates Endothelial Cell Tube Formation on Basement Membrane Matrix, Matrigel," *Exp. Cell Research* 199:56–62 (1992).

Klagsbrun and Soker, "VEGF/VPF: the angiogenesis factor found?" *Current Biology* 3:699–702 (1993)f.

Koch et al., "SH2and SH3 Domains: Elements That Control Interactions of Cytoplasmic Signaling Proteins," *Science* 252:668–674 (1991).

Kohler and Milstein, "Continuous cultures of fused cells secreting antibody of predefined specificity," *Nature* 256:495–497 (1975).

Korc et al., "Overexpression of the Epidermal Growth Factor Receptor in Human Pancreatic Cancer is Associated with Concomitant Increases in the Levels of Epidermal Growth Factor and Transforming Growth Factor Alpha," *J. Clin. Invest.* 90:1352–1360 (1992).

Krueger and Saito, "A human transmembrane protein–tyrosine–phosphatase, PTP, is expressed in brain and has an N–terminal receptor domain homologous to carbonic anhydrases," *Proc. Natl. Acad. Sci. USA* 89:7417–7421 (1992).

Kumabe et al., "Amplification of α–platelet–derived growth factor receptor gene lacking an exon coding for a portion of the extracellular region in a primary brain tumor of glial origin," *Oncogene* 7:627–633 (1992).

Lee and Donoghue, "Intracellular retention of membrane–anchored v–sis protein abrogates autocrine signal transduction," *Journal of Cell Biology* 118:1057–1070 (1992).

Macauley et al., "Autocrine function for insulin–like growth factor I in human small cell lung cancer cell lines and fresh tumor cells," *Cancer Research* 50:2511–2517 (1990).

Mariani et al., "Inhibition of angiogenesis by PCE 26806, a potent tyrosine kinase inhibitor," *Experimental Therapeutics—Proceedings of the American Association for Cancer Research* 35:381 at abstract No. 2268 (Mar. 1994).

Plate et al., "Vascular endothelial growth factor is potential tumor angiogenesis factor in human gilomas in vivo," *Nature* 359:845–848 (1992).

Plowman et al., "Receptor Tyrosine Kinases as Targets for Drug Intervention," *DN&P* 7(6):334–339 (1994).

Saito and Streuli,"Molecular Characterization of Protein Tyrosine Phosphatases," *Cell Growth & Differentiation* 2(1):59–65 (1991).

Sandberg–Nordqvist et al., "Characterization of Insulin–Like Growth Factor 1 in Human Primary Brain Tumors," *Cancer Research* 53:2475–2478 (1993).

Schlessinger and Ullrich, "Growth Factor Signalling by Receptor Tyrosine Kinases," *Neuron* 9:383–391 (1992).

Schuchter et al., "Successful Treatment of Murine Melanoma with Bryostatin 1," *Cancer Research* 51:682–687 (1991).

Shibuya et al., "Nucleotide sequence and expression of a novel human receptor–type tyrosine kinase gene (flt) closely realted to the fms family," *Oncogene* 5:519–524 (1990).

Shweiki et al., "Vascular endothelial growth factor induced by hypoxia may mediate hypoxia–initiated angiogenesis," *Nature* 359:843–845 (1992).

Slamon et al., "Studies of the HER–2/neu Proto–oncogene in Human Breast and Ovarian Cancer," *Science* 244:707–712 (1989).

Songyang et al., "SH2 Domains Recognize Specific Phosphopeptide Sequences," *Cell* 72:767–778 (1993).

Songyang et al., "Specific Motifis Recognized by the SH2 Domains of Csk, 3BP2, fps/fes, GRB–2, HCP, SHC, Syk and Vav," *Molecular and Cellular Biology* 14:2777–2785 (1994).

Superti–Furga et al., "A functional screen in yeast for regulators and antagonizers of heterologous protein tyrosine kinases," *nature Biotech* 14:600–605 (1996).

Superti–Furga et al., "Csk inhibition of c–Src activity requires both the SH2 and SH3 domains of Src," *EMBO J.* 12:2625–2634 (1993).

Takano et al., "Inhibition of angiogenesis by a novel diaminoanthraquinone that inhibits protein kinase C," *Mol. Bio. Cell* 4:358A at abstract No. 2076 (1993).

Torp et al., "Expression of the Epidermal Growth Factor Receptor Gene in Human Brain Metastases" *AMPIS* 100:713–716 (1992).

Tuzi et al., "Expression of growth factor receptors in human brain tumours," *Br. J. Cancer* 63:227–233 (1991).

Vaisman et al., "Characterization of the Receptors for Vascular Endothelial Growth Factor," *J. Biol. Chem.* 265:19461–19466 (1990).

Weidner et al., "Tumor Angiogenesis and Metastasis—Correlation in Invasive Breast Carcinoma," *New England J. Medicine* 324:1–7 (1991).

Wright et al., "Inhibition of Angiogenesis in Vitro and In Ovo With an Inhibitor of Cellular Protein Kinases, MDL 27032," *J. Cellular Physiology* 152:448–457 (1992).

\* cited by examiner

METHODS OF MODULATING PROTEIN TYROSINE KINASE FUNCTION WITH SUBSTITUTED INDOLINONE COMPOUNDS

RELATED APPLICATIONS

This application is a continuation of Ser. No. 09/407,164, filed Sep. 28, 1999 and claims priority to Ser. No. 60/102,178, filed Sep. 28, 1998, and to Ser. No. 09/129,256, filed Aug. 4, 1998, all of which are hereby incorporated by reference herein in their entirety, including any drawings.

BACKGROUND OF THE INVENTION

The following description of the background of the invention is provided to aid in understanding the invention, but is not admitted to describe or constitute prior art to the invention.

Cellular signal transduction is a fundamental mechanism whereby extracellular stimuli are relayed to the interior of cells and subsequently regulate diverse cellular processes. One of the key biochemical mechanisms of signal transduction involves the reversible phosphorylation of proteins. Phosphorylation of polypeptides regulates the activity of mature proteins by altering their structure and function. Phosphate most often resides on the hydroxyl moiety (—OH) of serine, threonine, or tyrosine amino acids in proteins.

Enzymes that mediate phosphorylation of cellular effectors generally fall into two classes. The first class consists of protein kinases which transfer a phosphate moiety from adenosine triphosphate to protein substrates. The second class consists of protein phosphatases which hydrolyze phosphate moieties from phosphoryl protein substrates. The converse functions of protein kinases and protein phosphatases balance and regulate the flow of signals in signal transduction processes.

Protein kinases and protein phosphatases are generally divided into two groups—receptor and non-receptor type proteins. Most receptor-type protein tyrosine phosphatases contain two conserved catalytic domains, each of which encompasses a segment of 240 amino acid residues. Saito et al., 1991, *Cell Growth and Diff* 2:59–65. Receptor protein tyrosine phosphatases can be subclassified further based upon the amino acid sequence diversity of their extracellular domains. Saito et al., supra; Krueger et al., 1992, *Proc. Natl. Acad. Sci. USA* 89:7417–7421.

Protein kinases and protein phosphatases are also typically divided into three classes based upon the amino acids they act upon. Some catalyze the addition or hydrolysis of phosphate on serine or threonine only, some catalyze the addition or hydrolysis of phosphate on tyrosine only, and some catalyze the addition or hydrolysis of phosphate on serine, threonine, and tyrosine.

Tyrosine kinases can regulate the catalytic activity of other protein kinases involved in cell proliferation. Protein kinases with inappropriate activity are also involved in some types of cancer. Abnormally elevated levels of cell proliferation are associated with receptor and non-receptor protein kinases with unregulated activity.

In addition to their role in cellular proliferation, protein kinases are thought to be involved in cellular differentiation processes. Cell differentiation occurs in some cells upon nerve growth factor (NGF) or epidermal growth factor (EGF) stimulation. Cellular differentiation is characterized by rapid membrane ruffling, cell flattening, and increases in cell adhesion. Chao, 1992, *Cell* 68:995–997.

In an effort to discover novel treatments for cancer and other diseases, biomedical researchers and chemists have designed, synthesized, and tested molecules that inhibit the function of protein kinases. Some small organic molecules form a class of compounds that modulate the function of protein kinases. Examples of molecules that have been reported to inhibit the function of protein kinases are bis-monocyclic, bicyclic or heterocyclic aryl compounds (PCT WO 92/20642), vinylene-azaindole derivatives (PCT WO 94/14808), 1-cyclopropyl-4-pyridyl-quinolones (U.S. Pat. No. 5,330,992), styryl compounds (by Levitzki, et al., U.S. Pat. No. 5,217,999, and entitled "Styryl Compounds which Inhibit EGF Receptor Protein Tyrosine Kinase), styryl-substituted pyridyl compounds (U.S. Pat. No. 5,302,606), certain quinazoline derivatives (EP Application No. 0 566 266 A1), seleoindoles and selenides (PCT WO 94/03427), tricyclic polyhydroxylic compounds (PCT WO 92/21660), and benzylphosphonic acid compounds (PCT WO 91/15495).

The compounds that can traverse cell membranes and are resistant to acid hydrolysis are potentially advantageous therapeutics as they can become highly bioavailable after being administered orally to patients. However, many of these protein kinase inhibitors only weakly inhibit the function of protein kinases. In addition, many inhibit a variety of protein kinases and will therefore cause multiple side-effects as therapeutics for diseases.

Despite the significant progress that has been made in developing compounds for the treatment of cancer, there remains a need in the art to identify the particular structures and substitution patterns that form the compounds capable of modulating the function of particular protein kinases.

SUMMARY OF THE INVENTION

The present invention is directed in part towards indolinone compounds and methods of modulating the function of protein tyrosine kinases with the indolinone compounds. The methods incorporate cells that express a protein tyrosine kinase. In addition, the invention describes methods of preventing and treating protein tyrosine kinases-related abnormal conditions in organisms with a compound identified by the methods described herein. Furthermore, the invention pertains to pharmaceutical compositions comprising compounds identified by methods of the invention.

The present invention features indolinone compounds that potently inhibit protein kinases and related products and methods. Inhibitors of protein kinases can be obtained by adding chemical substituents to an indolinone compound. The compounds of the invention represent a new generation of therapeutics for diseases associated with one or more functional or non-functional protein kinases. Neurodegenerative diseases and certain types of cancer fall into this class of diseases. The compounds can be modified such that they are specific to their target or targets and will subsequently cause few side effects and thus represent a new generation of potential cancer therapeutics. These properties are significant improvements over the currently utilized cancer therapeutics that cause multiple side effects and deleteriously weaken patients.

It is believed the compounds of the invention will minimize or obliterate solid tumors by inhibiting the activity of the protein tyrosine kinases, or will at least modulate or inhibit tumor growth and/or metastases. Protein tyrosine kinases regulate proliferation of blood vessels during angiogenesis, among other functions. Increased rates of angiogenesis accompany cancer tumor growth in cells as cancer tumors must be nourished by oxygenated blood during growth. Therefore, inhibition of the protein tyrosine kinase and the corresponding decreases in angiogenesis will starve tumors of nutrients and most likely obliterate them.

While a precise understanding of the mechanism by which compounds inhibit PTKs (e.g., the fibroblast growth factor receptor 1 [FGFR1]) is not required in order to practice the present invention, the compounds are believed to interact with the amino acids of the PTKs' catalytic region. PTKs typically possess a bi-lobate structure, and ATP appears to bind in the cleft between the two lobes in a region where the amino acids are conserved among PTKs; inhibitors of PTKs are believed to bind to the PTKs through non-covalent interactions such as hydrogen bonding, Van der Waals interactions, and ionic bonding, in the same general region that ATP binds to the PTKs. More specifically, it is thought that the oxindole component of the compounds of the present invention binds in the same general space occupied by the adenine ring of ATP. Specificity of an indolinone PTK inhibitor for a particular PTK may be conferred by interactions between the constituents around the oxindole core with amino acid domains specific to individual PTKs. Thus, different indolinone substituents may contribute to preferential binding to particular PTKs. The ability to select those compounds active at different ATP binding sites makes them useful in targeting any protein with such a site, not only protein tyrosine kinases, but also serine/threonine kinases and protein phosphatases. Thus, such compounds have utility for in vitro assays on such proteins and for in vivo therapeutic effect through such proteins.

Thus, in a first aspect, the invention provides an indolinone compound having a structure set forth in formula I:

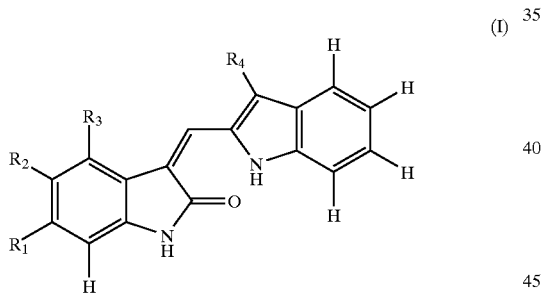

(I)

where
(a) $R_1$ is selected from the group consisting of hydrogen and halogen;
(b) $R_2$ is selected from the group consisting of
  (i) hydrogen;
  (ii) an amine of formula —$(X_1)_{n1}$—$NX_2X_3$, or an imine of formula —$(X_1)_{n1}$—N=$X_4$, where $X_1$ is selected from the group consisting of saturated or unsaturated alkyl and five-membered or six-membered aromatic, heteroaromatic, or aliphatic ring moieties and where n1 is 0, 1, or 2, and where $X_2$ and $X_3$ are independently selected from the group consisting of hydrogen, saturated or unsaturated alkyl, and five-membered or six-membered aromatic, heteroaromatic, or aliphatic ring moieties, or $X_2$ and $X_3$ taken together form a five-membered or six-membered heteroaliphatic or heteroaromatic ring, or where $X_4$ is an alkylene group optionally substituted with an aromatic or heteroaromatic monocyclic or bicyclic ring moiety;
  (iii) a halogen;
  (iv) a carboxylic acid of formula —$(X_6)_{n6}$—COOH or an ester of formula —$(X_7)_{n7}$—COO—$X_8$, where $X_6$, $X_7$, and $X_8$ are independently selected from the group consisting of alkyl and five-membered or six-membered aromatic, heteroaromatic, aliphatic, or heteroaliphatic ring moieties, and where n6 and n7 are each independently 0, 1, or 2;
  (v) a sulfonamide of formula —$(X_{17})_{n17}$—$SO_2NX_{18}X_{19}$, where $X_{17}$ is selected from the group consisting of alkyl and five-membered or six-membered aromatic, heteroaromatic, aliphatic, or heteroaliphatic ring moieties optionally substituted with one or more substituents independently selected from the group consisting of alkyl, halogen, trihalomethyl, carboxylate, amino, nitro, or ester, and where n17 is 0, 1, or 2, and where $X_{18}$ and $X_{19}$ are each independently selected from the group consisting of alkyl and five-membered or six-membered aromatic, heteroaromatic, aliphatic, or heteroaliphatic ring moieties optionally substituted with one or more substituents independently selected from the group consisting of alkyl, halogen, trihalomethyl, carboxylate, amino, nitro, or ester, or where $X_{18}$ and $X_{19}$ taken together form a five-membered or six-membered aliphatic or heteroaliphatic ring optionally substituted with one or more substituents independently selected from the group consisting of alkyl, halogen, trihalomethyl, carboxylate, amino, nitro, and ester;
  (vi) an aldehyde of formula —$(X_{20})_{n20}$—C(O)H where $X_{20}$ is selected from the group consisting of saturated or unsaturated alkyl and five-membered or six-membered aromatic, heteroaromatic, aliphatic, or heteroaliphatic ring moieties, where the ring is optionally substituted with one or more substituents independently selected from the group consisting of alkyl, halogen, trihalomethyl, carboxylate, amino, nitro, and ester, and where n20 is 0, 1, or 2;
  (vii) an amide of formula —$(X_{12})_{n12}$—$NHCOX_{13}$, or of formula —$(X_{14})_{n14}$—$CONX_{15}X_{16}$, where $X_{12}$ and $X_{14}$ are each independently selected from the group consisting of alkyl and five-membered or six-membered aromatic, heteroaromatic, aliphatic, or heteroaliphatic ring moieties, where the ring moiety is optionally substituted with one or more substituents independently selected from the group consisting of alkyl, halogen, trihalomethyl, carboxylate, amino, nitro, and ester and where n12 and n14 are independently 0, 1, or 2, and where $X_{13}$, $X_{15}$, and $X_{16}$ are each independently selected from the group consisting of hydrogen, alkyl, hydroxyl, and five-membered or six-membered aromatic, heteroaromatic, aliphatic, or heteroaliphatic ring moieties, where the ring is optionally substituted with one or more substituents independently selected from the group consisting of alkyl, halogen, trihalomethyl, carboxylate, amino, nitro, and ester; and
  (viii) a sulfone of formula —$(X_{21})_{n21}$—$SO_2$—$X_{22}$, where $X_{21}$ and $X_{22}$ are independently selected from the group consisting of saturated or unsaturated alkyl and five-membered or six-membered aromatic, heteroaromatic, aliphatic, or heteroaliphatic ring moieties, where the ring is optionally substituted with one or more substituents independently selected from the group consisting of alkyl, halogen, trihalomethyl, carboxylate, amino, nitro, and ester, and where n21 is 0, 1, or 2; and (c) $R_3$ and $R_4$ are each independently selected from the group consisting of
   (i) hydrogen;
   (ii) saturated or unsaturated alkyl optionally substituted with substituents selected from the group consisting of halogen, trihalomethyl, carboxylate, amino, nitro, ester, and a five-membered or six-membered aromatic, heteroaromatic, aliphatic, or heteroaliphatic ring moiety, where the ring moiety is optionally substituted with one, two, or three substituents independently selected from the group consisting of alkyl, halogen, trihalomethyl, carboxylate, amino, nitro, and ester moieties;
   (iii) an aromatic or heteroaromatic ring optionally substituted with one, two, or three substituents independently selected from the group consisting of alkyl, alkoxy, halogen, trihalomethyl, carboxylate, amino, nitro, and ester moieties;
   (iv) an aliphatic or heteroaliphatic ring optionally substituted with one, two, or three substituents independently selected from the group consisting of alkyl, alkoxy, halogen, trihalomethyl, carboxylate, amino, nitro, ester, and an aromatic or heteroaromatic ring optionally substituted with one, two, or three substituents independently selected from the group consisting of alkyl, alkoxy, halogen, trihalomethyl, carboxylate, amino, nitro, and ester moieties.

The term "compound" refers to the compound or a pharmaceutically acceptable salt, ester, amide, prodrug, isomer, or metabolite, thereof.

The term "pharmaceutically acceptable salt" refers to a formulation of a compound that does not abrogate the biological activity and properties of the compound. Pharmaceutical salts can be obtained by reacting a compound of the invention with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "prodrug" refers to an agent that is converted into the parent drug in vivo. Prodrugs may be easier to administer than the parent drug in some situations. For example, the prodrug may be bioavailable by oral administration but the parent is not, or the prodrug may improve solubility to allow for intravenous administration.

The term "indolinone" is used as that term is commonly understood in the art and includes a large subclass of substituted or unsubstituted compounds that are capable of being synthesized from an aldehyde moiety and a oxindole moiety.

The term "oxindole" refers to an oxindole compound substituted with chemical substituents. Oxindole compounds are of the general structure:

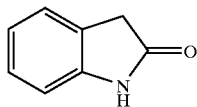

The term "substituted", in reference to the invention, refers to an oxindole compound that is derivatized with any number of chemical substituents.

The term "saturated alkyl" refers to an alkyl moiety that does not contain any alkene or alkyne moieties. The alkyl moiety may be branched, non-branched, or cyclic.

The term "unsaturated alkyl" refers to an alkyl moiety that contains at least one alkene or alkyne moiety. The alkyl moiety may be branched, non-branched, or cyclic.

The term "aromatic" refers to an aromatic group which has at least one ring having a conjugated pi electron system and includes both carbocyclic aryl (e.g., phenyl) and heterocyclic aryl groups (e.g., pyridine). The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon. The term "heteroaromatic" refers to an aromatic group which contains at least one heterocyclic ring.

The term "aliphatic ring" refers to a compound which contains one or more covalently closed ring structures, and that at least one of the atoms forming the backbone is a saturated carbon atom (e.g., cyclohexane). The term "heteroaliphatic ring" refers to a ring system in which at least one of the atoms forming the backbone is a heteroatom (e.g., tetrahydropyran).

The term "amine" refers to a chemical moiety of formula $NR_1R_2$ where $R_1$ and $R_2$ are independently selected from the group consisting of hydrogen, saturated or unsaturated alkyl, and five-membered or six-membered aryl or heteroaryl ring moieties, where the ring is optionally substituted with one or more substituents independently selected from the group consisting of alkyl, halogen, trihalomethyl, carboxylate, nitro, and ester moieties.

The term "imine" refers to a chemical moiety of formula $—N=R_1$ where $R_1$ is selected from the group consisting of hydrogen, saturated or unsaturated alkyl, and aryl or heteroaryl ring moieties (monocyclic or bicyclic), where the ring is optionally substituted with one or more substituents independently selected from the group consisting of alkyl, halogen, trihalomethyl, carboxylate, nitro, and ester moieties.

The term "halogen" refers to an atom selected from the group consisting of fluorine, chlorine, bromine, and iodine. The term "trihalomethyl" refers to the $—CX_3$ group, where X is a halogen.

The term "carboxylic acid" refers to a chemical moiety with formula $—(R)_n—COOH$, where R is selected from the group consisting of saturated or unsaturated alkyl and five-membered or six-membered aryl or heteroaryl moieties and where n is 0, 1, or 2.

The term "ester" refers to a chemical moiety with formula $—(R)_n—COOR'$, where R and R' are independently selected from the group consisting of saturated or unsaturated alkyl and five-membered or six-membered aryl or heteroaryl moieties and where n is 0, 1, or 2.

The term "aldehyde" refers to a chemical moiety with formula $—(R)_n—CHO$, where R is selected from the group consisting of saturated or unsaturated alkyl and five-membered or six-membered aryl or heteroaryl moieties and where n is 0, 1, or 2.

The term "sulfone" refers to a chemical moiety with formula $—SO_2—R$, where R is selected from the group consisting of saturated or unsaturated alkyl and five-membered. or six-membered aryl or heteroaryl moieties.

The term "acyl" refers to chemical moieties of the general formula $—C(O)R$. When R is hydrogen the molecule containing the acyl group is an aldehyde. When R is an alkyl, an aliphatic ring, or an aromatic ring, then the molecule containing the acyl group is a ketone.

In preferred embodiments, in the indolinone compound of formula I, $R_1$ is selected from the group consisting of hydrogen and halogen, more preferrably hydrogen and chlorine; $R_2$ is selected from the group consisting of

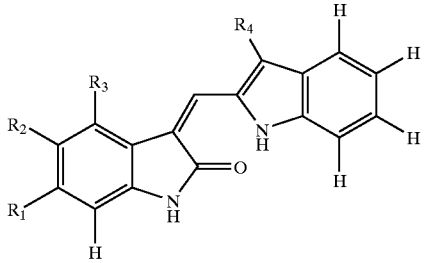

hydrogen, —SO₂NXY, —COOH, —C(O)X, NXY, and halogen, where X and Y are each independently selected from the group consisting of hydrogen and alkyl; and $R_3$ and $R_4$ are each independently selected from the group consisting of hydrogen and alkyl, more preferably hydrogen and methyl. More preferably $R_2$ is selected from the group consisting of

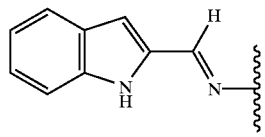

hydrogen, —SO₂NH₂, —COOH, —C(O)CH₃, NH₂, chlorine, and bromine.

The preferred indolinone compounds of the invention are listed in Table 1.

TABLE 1

| Compound Number | Compound Name |
|---|---|
| IN-001 | 5-methyl-3-(3-methyl-1H-indol-2-ylmethylene)-1,3-dihydro-indol-2-one |
| IN-002 | 3-(3-methyl-1H-indol-2-ylmethylene)-2-oxo-2,3-dihydro-1H-indol-5-sulfonic acid amide |
| IN-003 | 3(3-methyl-1H-indol-2-ylmethylene)-2-oxo-2,3-dihydro-1H-indole-5-sulfonic acid methylamide |
| IN-004 | 3-(3-methyl-1H-indole-2-ylmethylene)-2-oxo-2,3-dihydro-1H-indole-5-sulfonic acid dimethylamide |
| IN-005 | 3(3-methyl-1H-indol-2-ylmethylene)-2-oxo-2,3-dihydro-1H-indole-5-carboxylic acid |
| IN-006 | 5-acetyl-3-(3-methyl-1H-indol-2-ylmethylene)-1,3-dihydro-indol-2-one |
| IN-007 | 5-acetyl-3-(1H-indol-2-ylmethylene)-1,3-dihydro-indol-2-one |
| IN-008 | 3-(1H-indol-2-ylmethylene)-2-oxo-2,3-dihydro-1H-indol-5-sulfonic acid amide |
| IN-009 | 5-amino-3-(1H-indol-2-ylmethylene)-1,3-dihydro-indol-2-one |
| IN-010 | 3-(1H-indol-2-ylmethylene)-2-oxo-2,3-dihydro-1H-indole-5-carboxylic acid |
| IN-011 | 6-chloro-3-(1H-indol-2-ylmethylene)-1,3-dihydro-indol-2-one |
| IN-012 | 3-(1H-indol-2-ylmethylene)-1,3-dihydro-indol-2-one |
| IN-013 | 5-chloro-3-(1H-indol-2-ylmethylene)-1,3-dihydro-indol-2-one |
| IN-014 | 5-bromo-3-(1H-indol-2-ylmethylene)-1,3-dihydro-indol-2-one |
| IN-015 | 3-(1H-indol-2-ylmethylene)-4-methyl-1,3-dihydro-indol-2-one |
| IN-016 | 3-(3-methyl-1H-indol-2-ylmethylene)-1,3-dihydro-indol-2-one |
| IN-017 | 5-chloro-3-(3-methyl-1H-indol-2-ylmethylene)-1,3-dihydro-indol-2-one |
| IN-018 | 5-bromo-3-(3-methyl-1H-indol-2-ylmethylene)-1,3-dihydro-indol-2-one |
| IN-019 | 4-methyl-3-(3-methyl-1H-indol-2-ylmethylene)-1,3-dihydro-indol-2-one |
| IN-020 | 3-(1H-indol-2-ylmethylene)-5[(1H-indol-2-ylmethylene)-amino]-1,3-dihydro-indol-2-one |

The above compounds have the structure of formula X, with the substituents as defined in Table 2.

TABLE 2

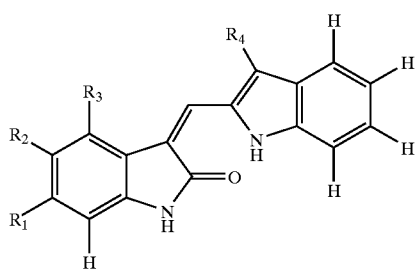

(X)

| Compound Number | $R_1$ | $R_2$ | $R_3$ | $R_4$ |
|---|---|---|---|---|
| IN-001 | H | CH₃ | H | CH₃ |
| IN-002 | H | SO₂NH₂ | H | CH₃ |
| IN-003 | H | SO₂NHCH₃ | H | CH₃ |
| IN-004 | H | SO₂N(CH₃)₂ | H | CH₃ |
| IN-005 | H | COOH | H | CH₃ |
| IN-006 | H | C(O)H | H | CH₃ |
| IN-007 | H | C(O)H | H | H |
| IN-008 | H | SO₂NH₂ | H | H |
| IN-009 | H | NH₂ | H | H |
| IN-010 | H | COOH | H | H |
| IN-011 | Cl | H | H | H |
| IN-012 | H | H | H | H |
| IN-013 | H | Cl | H | H |
| IN-015 | H | Br | CH₃ | H |
| IN-016 | H | H | H | CH₃ |
| IN-017 | H | Cl | H | CH₃ |
| IN-018 | H | Br | H | CH₃ |
| IN-019 | H | H | CH₃ | CH₃ |
| IN-020 | H | 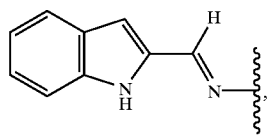 | H | H |

In another aspect, the invention features an indolinone compound having a structure set forth in formula I:

(I)

[Structure of formula I]

where
(a) $R_1$ is selected from the group consisting of hydrogen and chlorine;
(b) $R_2$ is selected from the group consisting of

[Structure]

hydrogen, —SO₂NH₂, —COOH, —C(O)CH₃, NH₂, chlorine, and bromine; and (c) R₃ and R₄ are each independently selected from the group consisting of hydrogen and methyl. The indolinone compounds contemplated by this aspect of the invention are set forth in Table 1, above.

In another aspect, the invention provides a combinatorial library of at least 10 indolinone compounds that can be formed by reacting an oxindole with an aldehyde, where the oxindole has a structure set forth in formula II

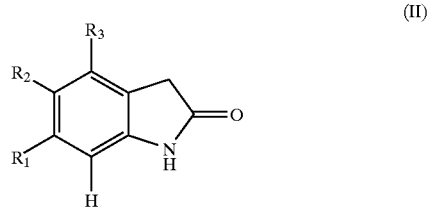

(II)

and where the aldehyde has a structure set forth in formula III

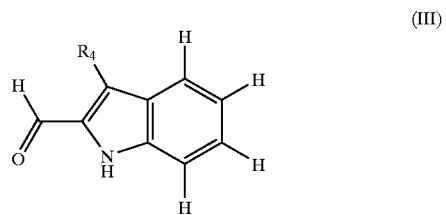

(III)

with R₁–R₄ are as set forth herein.

A "combinatorial library" refers to all the compounds formed by the reaction of each compound of one dimension with a compound in each of the other dimensions in a multi-dimensional array of compounds. In the context of the present invention, the array is two dimensional and one dimension represents all the oxindoles of the invention and the second dimension represents all the aldehydes of the invention. Each oxindole may be reacted with each and every aldehyde in order to form an indolinone compound. All indolinone compounds formed in this way are within the scope of the present invention. Also within the scope of the present invention are smaller combinatorial libraries formed by the reaction of some of the oxindoles with all of the aldehydes, all of the oxindoles with some of the aldehydes, or some of the oxindoles with some of the aldehydes.

The oxindole in the above combinatorial library is preferably selected from the group consisting of 2-oxindole, 5-chloro-2-oxindole, 6-chloro-2-oxindole, 5-bromo-2-oxindole, 4-methyl-2-oxindole, 5-methyl-2-oxindole, 5-aminosulfonyl-2-oxindole, 5-methylaminosulfonyl-2-oxindole, 5-dimethylaminosulfonyl-2-oxindole, 5-carboxy-2-oxindole, 5-amino-2-oxindole, and 5-acetyl-2-oxindole. The aldehyde is preferrably selected from the group consisting of indole-2-carbaldehyde and 3-methyl-indole-2carbaldehyde.

Another aspect of the invention provides for a method for synthesizing an indolinone compound of formula I, as described herein, comprising the step of reacting a first reactant with a second reactant in a solvent and in the presence of a base at elevated temperatures, where the first reactant is an oxindole having the structure set forth in formula II and the second reactant is an aldehyde, having a structure set forth in formula III, as those formulae are described herein.

The first reactant is preferably an oxindole selected from the group consisting of 2-oxindole, 5-chloro-2-oxindole, 6-chloro-2-oxindole, 5-bromo-2-oxindole, 4-methyl-2-oxindole, 5-methyl-2-oxindole, 5-aminosulfonyl-2-oxindole, 5-methylaminosulfonyl-2-oxindole, 5-dimethylaminosulfonyl-2-oxindole, 5-carboxy-2-oxindole, 5-amino-2-oxindole, and 5-acetyl-2-oxindole, and the second reactant is preferably an aldehyde selected from the group consisting of indole-2-carbaldehyde and 3-methyl-indole-2-carbaldehyde.

To synthesize the compounds of the invention a base may be used. The base is preferably a nitrogen base or an inorganic base. "Nitrogen bases" are commonly used in the art and are selected from acyclic and cyclic amines. Examples of nitrogen bases include, but are not limited to, ammonia, methylamine, trimethylamine, triethylamine, aniline, 1,8-diazabicyclo[5.4.0]undec-7-ene, diisopropylethylamine, pyrrolidine, and piperidine. "Inorganic bases" are bases that do not contain any carbon atoms. Examples of inorganic bases include, but are not limited to, hydroxide, phosphate, bisulfate, hydrosulfide, and amide anions. Those skilled in the art know which nitrogen base or inorganic base would match the requirements of the reaction conditions. In certain embodiments of the invention, the base used may be pyrrolidine or piperidine. In other embodiments the base may be the hydroxide anion, preferably used as its sodium or potassium salt.

The synthesis of the compounds of the invention takes place in a solvent. The solvent of the reaction is preferably a protic solvent or an aprotic solevent. "Protic solvents" are those that are capable of donating a proton to a solute. Examples of protic solvents include, but are not limited to, alcohols and water. "Aprotic solvents" are those solvents that, under normal reaction conditions, do not donate a proton to a solute. Typical organic solvents, such as hexane, toluene, benzene, methylene chloride, dimethylformamide, chloroform, tetrahydrofuran, are some of the examples of aprotic solvents. Other aprotic solvents are also within the scope of used by the present invention. In some preferred embodiments, the solvent of the reaction is an alcohol, which may preferably be isopropanol or most preferably ethanol. Water is another preferred protic solvent. Dimethylformamide, known in the chemistry art as DMF, is a preferred aprotic solvent.

The synthetic method of the invention calls for the reaction to take place at elevated temperatures which are temperatures that are greater than room temperature. More preferably, the elevated temperature is preferably about 30–150° C., more preferably is about 80–100° C., and most preferably is about 80–90° C., which is about the temperature at which ethanol boils (i.e., the boiling point of ethanol). By "about" a certain temperature it is meant that the temperature range is preferably within 10° C. of the listed temperature, more preferably within 5° C. of the listed temperature, and most preferably within 2° C. of the listed temperature. Therefore, by way of example, by "about 80° C." it is meant that the temperature range is preferably 80±10° C., more preferably 80±5° C., and most preferably 80±2° C.

The synthetic method of the invention may be accompanied by the step of screening a library for a compound of the desired activity and structure—thus, providing a method of synthesis of a compound by first screening for a compound having the desired properties and then chemically synthesizing that compound.

In another aspect, the invention features a pharmaceutical composition comprising (i) a physiologically acceptable carrier, diluent, or excipient; and (ii) an indolinone compound as described herein.

The term "pharmaceutical composition" refers to a mixture of an indolinone compound of the invention with other chemical components, such as diluents, excipients, or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "physiologically acceptable" defines a carrier or diluent that does not abrogate the biological activity and properties of the compound.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The invention also features a method of modulating the function of a protein tyrosine kinase with an indolinone compound of the invention, comprising the step of contacting cells expressing the protein tyrosine kinase with the compound.

The term "function" refers to the cellular role of a protein tyrosine kinase. The protein tyrosine kinase family includes members that regulate many steps in signaling cascades, including cascades controlling cell growth, migration, differentiation, gene expression, muscle contraction, glucose metabolism, cellular protein synthesis, and regulation of the cell cycle.

The term "catalytic activity", in the context of the invention, defines the rate at which a protein kinase phosphorylates a substrate. Catalytic activity can be measured, for example, by determining the amount of a substrate converted to a product as a function of time. Phosphorylation of a substrate occurs at the active-site of a protein kinase. The active-site is normally a cavity in which the substrate binds to the protein kinase and is phosphorylated.

The term "substrate" as used herein refers to a molecule phosphorylated by a protein tyrosine kinase. The substrate is preferably a peptide and more preferably a protein.

The term "activates" refers to increasing the cellular function of a protein kinase. The protein kinase function is preferably the interaction with a natural binding partner and most preferably catalytic activity.

The term "inhibit" refers to decreasing the cellular function of a protein kinase. The protein kinase function is preferably the interaction with a natural binding partner and most preferably catalytic activity.

The term "modulates" refers to altering the function of a protein kinase by increasing or decreasing the probability that a complex forms between a protein kinase and a natural binding partner. A modulator preferably increases the probability that such a complex forms between the protein kinase and the natural binding partner, more preferably increases or decreases the probability that a complex forms between the protein kinase and the natural binding partner depending on the concentration of the compound exposed to the protein kinase, and most preferably decreases the probability that a complex forms between the protein kinase and the natural binding partner. A modulator preferably activates the catalytic activity of a protein kinase, more preferably activates or inhibits the catalytic activity of a protein kinase depending on the concentration of the compound exposed to the protein kinase, or most preferably inhibits the catalytic activity of a protein kinase.

The term "complex" refers to an assembly of at least two molecules bound to one another. Signal transduction complexes often contain at least two protein molecules bound to one another.

The term "natural binding partner" refers to polypeptides that bind to a protein kinase in cells. Natural binding partners can play a role in propagating a signal in a protein kinase signal transduction process. A change in the interaction between a protein kinase and a natural binding partner can manifest itself as an increased or decreased probability that the interaction forms, or an increased or decreased concentration of the protein kinase/natural binding partner complex.

A protein kinase natural binding partner can bind to a protein kinase's intracellular region with high affinity. High affinity represents an equilibrium binding constant on the order of $10^{-6}$ M or less. In addition, a natural binding partner can also transiently interact with a protein kinase intracellular region and chemically modify it. Protein kinase natural binding partners are chosen from a group that includes, but is not limited to, SRC homology 2 (SH2) or 3 (SH3) domains, other phosphoryl tyrosine binding (PTB) domains, guanine nucleotide exchange factors, protein phosphatases, and other protein kinases. Methods of determining changes in interactions between protein kinases and their natural binding partners are readily available in the art.

The term "contacting" as used herein refers to mixing a solution comprising an indolinone compound of the invention with a liquid medium bathing the cells of the methods. The solution comprising the compound may also comprise another component, such as dimethylsulfoxide (DMSO), which facilitates the uptake of the indolinone compound or compounds into the cells of the methods. The solution comprising the indolinone compound may be added to the medium bathing the cells by utilizing a delivery apparatus, such as a pipet-based device or syringe-based device.

The indolinone compounds of the invention preferably modulate the activity of the protein tyrosine kinase in vitro. These compounds preferably show positive results in one or more in vitro assays for an activity corresponding to treatment of the disease or disorder in question (such as the assays described in the Examples below).

The invention also features a method of identifying indolinone compounds that modulate the function of protein tyrosine kinase, comprising the following steps: (a) contacting cells expressing the protein tyrosine kinase with the compound; and (b) monitoring an effect upon the cells. The effect upon the cells is preferably a change or an absence of a change in cell phenotype, more preferably it is a change or an absence of a change in cell proliferation, even more preferably it is a change or absence of a change in the catalytic activity of the protein tyrosine kinase, and most preferably it is a change or absence of a change in the interaction between the protein tyrosine kinase with a natural binding partner, as described herein.

The term "monitoring" refers to observing the effect of adding the compound to the cells of the method. The effect can be manifested in a change in cell phenotype, cell proliferation, protein kinase catalytic activity, or in the interaction between a protein kinase and a natural binding partner.

The term "effect" describes a change or an absence of a change in cell phenotype or cell proliferation. "Effect" can also describe a change or an absence of a change in the catalytic activity of the protein kinase. "Effect" can also describe a change or an absence of a change in an interaction between the protein kinase and a natural binding partner.

The term "cell phenotype" refers to the outward appearance of a cell or tissue or the function of the cell or tissue. Examples of cell phenotype are cell size (reduction or enlargement), cell proliferation (increased or decreased numbers of cells), cell differentiation (a change or absence of a change in cell shape), cell survival, apoptosis (cell death), or the utilization of a metabolic nutrient (e.g., glucose uptake). Changes or the absence of changes in cell phenotype are readily measured by techniques known in the art.

In a preferred embodiment, the invention features a method for identifying the indolinones of the invention, comprising the following steps: (a) lysing the cells to render a lysate comprising protein tyrosine kinase; (b) adsorbing the protein tyrosine kinase to an antibody; (c)incubating the adsorbed protein tyrosine kinase with a substrate or substrates; and (d) adsorbing the substrate or substrates to a solid support or antibody; where the step of monitoring the effect on the cells comprises measuring the phosphate concentration of the substrate or substrates.

The term "antibody" refers to an antibody (e.g., a monoclonal or polyclonal antibody), or antibody fragment, having specific binding affinity to protein tyrosine kinase or its fragment.

By "specific binding affinity" is meant that the antibody binds to target (protein tyrosine kinase) polypeptides with greater affinity than it binds to other polypeptides under specified conditions. Antibodies having specific binding affinity to a protein tyrosine kinase may be used in methods for detecting the presence and/or amount of a protein tyrosine kinase in a sample by contacting the sample with the antibody under conditions such that an immunocomplex forms and detecting the presence and/or amount of the antibody conjugated to the protein tyrosine kinase. Diagnostic kits for performing such methods may be constructed to include a first container containing the antibody and a second container having a conjugate of a binding partner of the antibody and a label, such as, for example, a radioisotope. The diagnostic kit may also include notification of an FDA approved use and instructions therefor.

The term "polyclonal" refers to antibodies that are heterogenous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

"Monoclonal antibodies" are substantially homogenous populations of antibodies to a particular antigen. They may be obtained by any technique which provides for the production of antibody molecules by continuous cell lines in culture. Monoclonal antibodies may be obtained by methods known to those skilled in the art. See, for example, Kohler, et al., *Nature* 256:495–497 (1975), and U.S. Pat. No. 4,376,110.

The term "antibody fragment" refers to a portion of an antibody, often the hypervariable region and portions of the surrounding heavy and light chains, that displays specific binding affinity for a particular molecule. A hypervariable region is a portion of an antibody that physically binds to the polypeptide target.

In yet another aspect, the invention features a method for treating a disease related to unregulated tyrosine kinase signal transduction, where the method includes the step of administering to a subject in need thereof a therapeutically effective amount of an indolinone compound as described herein.

The invention also features a method of regulating tyrosine kinase signal transduction comprising administering to a subject a therapeutically effective amount of an indolinone compound as described herein.

Furthermore, the invention features a method of preventing or treating an abnormal condition in an organism, where the abnormal condition is associated with an aberration in a signal transduction pathway characterized by an interaction between a protein kinase and a natural binding partner, where the method comprises the following steps: (a) administering an indolinone compound as described herein; and (b) promoting or disrupting the abnormal interaction. The organism is preferably a mammal and the abnormal condition is preferably cancer. The abnormal condition may also preferably be selected from the group consisting of hypertension, depression, generalized anxiety disorder, phobias, post-traumatic stress syndrome, avoidant personality disorder, sexual dysfunction, eating disorders, obesity, chemical dependencies, cluster headache, migraine, pain, Alzheimer's disease, obsessive-compulsive disorder, panic disorder, memory disorders, Parkinson's disease, endocrine disorders, vasospasm, cerebellar ataxia, and gastrointestinal tract disorders.

The term "aberration", in conjunction with a signal transduction process, refers to a protein kinase that is over- or under-expressed in an organism, mutated such that its catalytic activity is lower or higher than wild-type protein kinase activity, mutated such that it can no longer interact with a natural binding partner, is no longer modified by another protein kinase or protein phosphatase, or no longer interacts with a natural binding partner.

The term "promoting or disrupting the abnormal interaction" refers to a method that can be accomplished by administering a compound of the invention to cells or tissues in an organism. A compound can promote an interaction between a protein kinase and natural binding partners by forming favorable interactions with multiple atoms at the complex interface. Alternatively, a compound can inhibit an interaction between a protein kinase and natural binding partners by compromising favorable interactions formed between atoms at the complex interface.

The summary of the invention described above is non-limiting and other features and advantages of the invention will be apparent from the following description of the preferred embodiments, and from the claims.

DETAILED DESCRIPTION OF THE INVENTION

The present invention relates to compounds capable of regulating and/or modulating tyrosine kinase signal transduction and more particularly receptor and non-receptor tyrosine kinase signal transduction.

Receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects to the extracellular microenvironment). See, Schlessinger and Ullrich, 1992, Neuron 9:303–391.

It has been shown that tyrosine phosphorylation sites in growth factor receptors function as high-affinity binding sites for SH2 (src homology) domains of signaling molecules. Fantl et al., 1992, Cell 69:413–423; Songyang et al., 1994, Mol. Cell. Biol. 14:2777–2785); Songyang et al., 1993, Cell 72:767–778; and Koch et al., 1991, Science 252:668–678. Several intracellular substrate proteins that associate with receptor tyrosine kinases have been identified. They may be divided into two principal groups: (1) substrates which have a catalytic domain; and (2) substrates which lack such domain but serve as adapters and associate with catalytically active molecules. Songyang et al., 1993, Cell 72:767–778. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. Songyang et al., 1993, Cell 72:767–778. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Tyrosine kinase signal transduction results in, among other responses, cell proliferation, differentiation and metabolism. Abnormal cell proliferation may result in a wide array of disorders and diseases, including the development of neoplasia such as carcinoma, sarcoma, leukemia, glioblastoma, hemangioma, psoriasis, arteriosclerosis, arthritis and diabetic retinopathy (or other disorders related to uncontrolled angiogenesis and/or vasculogenesis).

This invention is therefore directed to compounds which regulate, modulate and/or inhibit tyrosine kinase signal transduction by affecting the enzymatic activity of the RTKs and/or the non-receptor tyrosine kinases and interfering with the signal transduced by such proteins. More particularly, the present invention is directed to compounds which regulate, modulate and/or inhibit the RTK and/or non-receptor tyrosine kinase mediated signal transduction pathways as a therapeutic approach to cure many kinds of solid tumors, including but not limited to carcinoma, sarcoma, leukemia, erythroblastoma, glioblastoma, meningioma, astrocytoma, melanoma and myoblastoma. Indications may include, but are not limited to brain cancers, bladder cancers, ovarian cancers, gastric cancers, pancreas cancers, colon cancers, blood cancers, lung cancers and bone cancers.

I. Target Diseases to be Treated by the Compounds of the Invention

The compounds described herein are useful for treating disorders related to unregulated tyrosine kinase signal transduction, including cell proliferative disorders, fibrotic disorders and metabolic disorders.

Cell proliferative disorders which can be treated or further studied by the present invention include cancers, blood vessel proliferative disorders and mesangial cell proliferative disorders.

Blood vessel proliferative disorders refer to angiogenic and vasculogenic disorders generally resulting in abnormal proliferation of blood vessels. The formation and spreading of blood vessels, or vasculogenesis and angiogenesis, respectively, play important roles in a variety of physiological processes such as embryonic development, corpus luteum formation, wound healing and organ regeneration. They also play a pivotal role in cancer development. Other examples of blood vessel proliferation disorders include arthritis, where new capillary blood vessels invade the joint and destroy cartilage, and ocular diseases, like diabetic retinopathy, where new capillaries in the retina invade the vitreous, bleed and cause blindness. Conversely, disorders related to the shrinkage, contraction or closing of blood vessels, such as restenosis, are also implicated.

Fibrotic disorders refer to the abnormal formation of extracellular matrix. Examples of fibrotic disorders include hepatic cirrhosis and mesangial cell proliferative disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis. Other fibrotic disorders implicated include atherosclerosis (see, below).

Mesangial cell proliferative disorders refer to disorders brought about by abnormal proliferation of mesangial cells. Mesangial proliferative disorders include various human renal diseases, such as glomerulonephritis, diabetic nephropathy, malignant nephrosclerosis, thrombotic microangiopathy syndromes, transplant rejection, and glomerulopathies. The PDGF-R has been implicated in the maintenance of mesangial cell proliferation. Floege et al., 1993, Kidney International 43:47S–54S.

PTKs have been associated with such cell proliferative disorders. For example, some members of the RTK family have been associated with the development of cancer. Some of these receptors, like the EGFR (Tuzi et al., 1991, Br. J. Cancer 63:227–233; Torp et al., 1992, APMIS 100:713–719) HER2/neu (Slamon et al., 1989, Science 244:707–712) and the PDGF-R (Kumabe et al., 1992, Oncogene 7:627–633) are overexpressed in many tumors and/or persistently activated by autocrine loops. In fact, in the most common and severe cancers these receptor overexpressions (Akbasak and Suner-Akbasak et al., 1992, J. Neurol. Sci. 111:119–133; Dickson et al., 1992, Cancer Treatment Res. 61:249–273; Korc et al., 1992, J. Clin. Invest. 90:1352–1360) and autocrine loops (Lee and Donoghue, 1992, J. Cell. Biol. 118:1057–1070; Korc et al., supra; Akbasak and Suner-Akbasak et al., supra) have been demonstrated. For example, the EGFR receptor has been associated with squamous cell carcinoma, astrocytoma, glioblastoma, head and neck cancer, lung cancer and bladder cancer. HER2 has been associated with breast, ovarian, gastric, lung, pancreas and bladder cancer. The PDGF-R has been associated with glioblastoma, lung, ovarian, melanoma and prostate cancer. The RTK c-met has been generally associated with hepatocarcinogenesis and thus hepatocellular carcinoma. Additionally, c-met has been linked to malignant tumor formation. More specifically, the RTK c-met has been associated with, among other cancers, colorectal, thyroid, pancreatic and gastric carcinoma, leukemia and lymphoma. Additionally, over-expression of the c-met gene has been detected in patients with Hodgkin's disease, Burkitt's disease, and the lymphoma cell line.

The IGF-IR, in addition to being implicated in nutritional support and in type-II diabetes, has also been associated with several types of cancers. For example, IGF-I has been implicated as an autocrine growth stimulator for several tumor types, e.g., human breast cancer carcinoma cells (Arteaga et al., 1989, *J. Clin. Invest.* 84:1418–1423) and small lung tumor cells (Macauley et al., 1990, *Cancer Res.* 50:2511–2517). In addition, IGF-I, integrally involved in the normal growth and differentiation of the nervous system, appears to be an autocrine stimulator of human gliomas. Sandberg-Nordqvist et al., 1993, *Cancer Res.* 53:2475–2478. The importance of the IGF-IR and its ligands in cell proliferation is further supported by the fact that many cell types in culture (fibroblasts, epithelial cells, smooth muscle cells, T-lymphocytes, myeloid cells, chondrocytes, osteoblasts, the stem cells of the bone marrow) are stimulated to grow by IGF-I. Goldring and Goldring, 1991, *Eukaryotic Gene Expression* 1:301–326. In a series of recent publications, Baserga even suggests that IGF-I-R plays a central role in the mechanisms of transformation and, as such, could be a preferred target for therapeutic interventions for a broad spectrum of human malignancies. Baserga, 1995, *Cancer Res.* 55:249–252; Baserga, 1994, *Cell* 79:927–930; Coppola et al., 1994; *Mol. Cell. Biol.* 14:4588–4595.

The association between abnormalities in RTKs and disease are not restricted to cancer, however. For example, RTKs have been associated with metabolic diseases like psoriasis, diabetes mellitus, wound healing, inflammation, and neurodegenerative diseases. These diseases include, but are not limited to hypertension, depression, generalized anxiety disorder, phobias, post-traumatic stress syndrome, avoidant personality disorder, sexual dysfunction, eating disorders, obesity, chemical dependencies, cluster headache, migraine, pain, Alzheimer's disease, obsessive-compulsive disorder, panic disorder, memory disorders, Parkinson's disease, endocrine disorders, vasospasm, cerebellar ataxia, and gastrointestinal tract disorders. For example, the EGF-R is indicated in corneal and dermal wound healing. Defects in the Insulin-R and the IGF-1R are indicated in type-II diabetes mellitus. A more complete correlation between specific RTKs and their therapeutic indications is set forth in Plowman et al., 1994, *DN&P* 7:334–339.

Not only receptor type tyrosine kinases, but also many cellular tyrosine kinases (CTKs) including src, abl, fps, yes, fyn, lyn, lck, blk, hck, fgr, yrk (reviewed by Bolen et al., 1992, *FASEB J.* 6:3403–3409) are involved in the proliferative and metabolic signal transduction pathway and thus in indications of the present invention. For example, mutated src (v-src) has been demonstrated as an oncoprotein ($pp60^{v-src}$) in chicken. Moreover, its cellular homolog, the proto-oncogene $pp60^{c-src}$ transmits oncogenic signals of many receptors. For example, overexpression of EGF-R or HER2/neu in tumors leads to the constitutive activation of $pp60^{c-src}$, which is characteristic for the malignant cell but absent from the normal cell. On the other hand, mice deficient for the expression of c-src exhibit an osteopetrotic phenotype, indicating a key participation of c-src in osteoclast function and a possible involvement in related disorders. Similarly, Zap 70 is implicated in T-cell signaling.

Furthermore, the identification of CTK modulating compounds to augment or even synergize with RTK aimed blockers is an aspect of the present invention.

Finally, both RTKs and non-receptor type kinases have been connected to hyperimmune disorders.

The compounds of the present invention are also effective in treating diseases that are related to the PYK-2 protein. This protein, its cellular function, and diseases related to them are set forth in detail in U.S. applications Ser. No. 08/357,642, filed Dec. 15, 1994, by Lev et al., and entitled "PYK2 RELATED PRODUCTS AND METHODS" (Lyon & Lyon Docket No. 209/070), and Ser. No. 08/460,626, filed Jun. 2, 1995, by Lev et al., and entitled "PYK2 RELATED PRODUCTS AND METHODS" (Lyon & Lyon Docket No. 211/121), which are hereby incorporated by reference herein in their entirety, including any drawings.

II. The KDR/FLK-1 Receptor and VEGF

Normal vasculogenesis and angiogenesis play important roles in a variety of physiological processes such as embryonic development, wound healing, organ regeneration and female reproductive processes such as follicle development in the corpus luteum during ovulation and placental growth after pregnancy. Folkman and Shing, 1992, *J. Biological Chem.* 267:10931–34. However, many diseases are driven by persistent unregulated or inappropriate angiogenesis. For example, in arthritis, new capillary blood vessels invade the joint and destroy the cartilage. In diabetes, new capillaries in the retina invade the vitreous, bleed and cause blindness. Folkman, 1987, in: *Congress of Thrombosis and Haemostasis* (Verstraete, et. al, eds.), Leuven University Press, Leuven, pp.583–596. Ocular neovascularization is the most common cause of blindness and dominates approximately twenty (20) eye diseases.

Moreover, vasculogenesis and/or angiogenesis have been associated with the growth of malignant solid tumors and metastasis. A tumor must continuously stimulate the growth of new capillary blood vessels for the tumor itself to grow. Furthermore, the new blood vessels embedded in a tumor provide a gateway for tumor cells to enter the circulation and to metastasize to distant sites in the body. Folkman, 1990, *J. Natl. Cancer Inst.* 82:4–6; Klagsbrunn and Soker, 1993, *Current Biology* 3:699–702; Folkman, 1991, *J. Natl., Cancer Inst.* 82:4–6; Weidner et al., 1991, *New Engl. J. Med.* 324:1–5.

Several polypeptides with in vitro endothelial cell growth promoting activity have been identified. Examples include acidic and basic fibroblastic growth factor (aFGF, bFGF), vascular endothelial growth factor (VEGF) and placental growth factor. Unlike aFGF and bFGF, VEGF has recently been reported to be an endothelial cell specific mitogen. Ferrara and Henzel, 1989, *Biochem. Biophys. Res. Comm.* 161:851–858; Vaisman et al., 1990, *J. Biol. Chem.* 265:19461–19566.

Thus, the identification of the specific receptors to which VEGF binds is an important advancement in the understanding of the regulation of endothelial cell proliferation. Two structurally closely related RTKs have been identified to bind VEGF with high affinity: the flt-1 receptor (Shibuya et al., 1990, *Oncogene* 5:519–524; De Vries et al., 1992, *Science* 255:989–991) and the KDR/FLK-1 receptor, discussed in the U.S. patent application Ser. No. 08/193,829. Consequently, it had been surmised that these RTKs may have a role in the modulation and regulation of endothelial cell proliferation.

Evidence, such as the disclosure set forth in copending U.S. application Ser. No. 08/193,829, strongly suggests that VEGF is not only responsible for endothelial cell proliferation, but also is a prime regulator of normal and pathological angiogenesis. See generally, Klagsburn and Soker, 1993, *Current Biology* 3:699–702; Houck et al., 1992, *J. Biol. Chem.* 267:26031–26037. Moreover, it has been shown that KDR/FLK-1 and flt-1 are abundantly expressed in the proliferating endothelial cells of a growing tumor, but not in the surrounding quiescent endothelial cells. Plate et al., 1992, *Nature* 359:845–848; Shweiki et al., 1992, *Nature* 359:843–845.

III. Identification of Agonists and Antagonists to the Kdr/Flk-1 Receptor

In view of the deduced importance of RTKs in the control, regulation and modulation of endothelial cell proliferation and potentially vasculogenesis and/or angiogenesis, many attempts have been made to identify RTK "inhibitors" using a variety of approaches. These include the use of mutant ligands (U.S. Pat. No. 4,966,849); soluble receptors and antibodies (Application No. WO 94/10202; Kendall and Thomas, 1994, *Proc. Natl. Acad. Sci. USA* 90:10705–10709; Kim et al., 1993, *Nature* 362:841–844); and RNA ligands (Jellinek et al., 1994, *Biochemistry* 33:10450–10456).

Furthermore, tyrosine kinase inhibitors (WO 94/03427; WO 92/21660; WO 91/15495; WO 94/14808; U.S. Pat. No. 5,330,992; Mariani et al., 1994, *Proc. Am. Assoc. Cancer Res.* 35:2268), and inhibitors acting on receptor tyrosine kinase signal transduction pathways, such as protein kinase C inhibitors have been identified (Schuchter et al., 1991, *Cancer Res.* 51:682–687); Takano et al., 1993, *Mol. Bio. Cell* 4:358A; Kinsella et al., 1992, *Exp. Cell Res.* 199:56–62; Wright et al., 1992, *J. Cellular Phys.* 152:448–57).

More recently, attempts have been made to identify small molecules which act as tyrosine kinase inhibitors. For example, bis monocyclic, bicyclic or heterocyclic aryl compounds (PCT WO 92/20642), vinylene-azaindole derivatives (PCT WO 94/14808) and 1-cyclopropyl-4-pyridyl-quinolones (U.S. Pat. No. 5,330,992) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1), seleoindoles and selenides (PCT WO 94/03427), tricyclic polyhydroxylic compounds (PCT WO 92/21660) and benzylphosphonic acid compounds (PCT WO 91/15495) have been described as compounds for use as tyrosine kinase inhibitors for use in the treatment of cancer.

Consequently, there is an unmet need for the identification and generation of effective small compounds which selectively inhibit the signal transduction of the KDR/FLK-1 receptor in order to effectively and specifically suppress vasculogenesis.

Some of the compounds of the present invention demonstrate excellent activity in biological assays and thus these compounds and related compounds are expected to be effective in treating Flk related disorders such as those driven by persistent unregulated or inappropriate angiogenesis.

IV. Pharmaceutical Formulations and Routes of Administration

The compounds described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., latest edition.

a) Routes of Administration

Suitable routes of administration may, for example, include oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections.

Alternately, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

b) Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant Polysorbate 80™, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the PTK modulating compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

c) Effective Dosage.

Pharmaceutical compositions suitable for use in the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

For any compound used in the methods of the invention, the therapeutically effective dose can be estimated initially from cell culture assays. For example, a dose can be formulated in animal models to achieve a circulating concentration range that includes the $IC_{50}$ as determined in cell culture (i.e., the concentration of the test compound which achieves a half-maximal inhibition of the PTK activity). Such information can be used to more accurately determine useful doses in humans.

Toxicity and therapeutic efficacy of the compounds described herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g., the concentration necessary to achieve 50–90% inhibition of the kinase using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

d) Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the polynucleotide for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

V. Biological Activity of the Indolinone Compounds of the Invention

The indolinone compounds of the present invention were tested for their ability to inhibit most of protein tyrosine kinase activity. The biological assays and results of these inhibition studies are reported herein. The methods used to measure indolinone compound modulation of protein kinase function are similar to those described in U.S. application Ser. No. 08/702,232, by Tang et al., and entitled "Indolinone Combinatorial Libraries and Related Products and Methods for the Treatment of Disease," filed Aug. 23, 1996, with respect to the high throughput aspect of the method. The Ser. No. 08/702,232 application is incorporated herein by reference in its entirety, including any drawings.

VI. Pharmaceutical Compositions and Administration of Indolinone Compounds of the Invention Methods of preparing pharmaceutical formulations of the compounds, methods of determining the amounts of compounds to be administered to a patient, and modes of administering compounds to an organism are disclosed in U.S. application Ser. No. 08/702,232, by Tang et al., and entitled "Indolinone Combinatorial Libraries and Related Products and Methods for the Treatment of Disease," filed Aug. 23, 1996, and International patent publication number WO 96/22976, by Buzzetti et al., and entitled "Hydrosoluble 3-Arylidene-2-Oxindole Derivatives as Tyrosine Kinase Inhibitors," published Aug. 1, 1996, both of which are incorporated herein by reference in their entirety, including any drawings. Those skilled in the art will appreciate that such descriptions are applicable to the present invention and can be easily adapted to it.

EXAMPLES

The examples below are non-limiting and are merely representative of various aspects and features of the present invention. The examples describe methods for synthesizing compounds of the invention and methods for measuring an effect of a compound on the function of protein tyrosine kinases.

The cells used in the methods are commercially available. The nucleic acid vectors harbored by the cells are also commercially available and the sequences of genes for the various protein kinases are readily accessible in sequence data banks. Thus, a person of ordinary skill in the art can readily recreate the cell lines in a timely manner by combining the commercially available cells, the commercially available nucleic acid vectors, and the protein kinase genes using techniques readily available to persons of ordinary skill in the art.

Example 1

Procedures for Synthesizing the Substituted Indolinone Compounds of the Invention Compound IN-001

5-Methyl-3-(3-methyl-1H-indol-2-ylmethylene)-1,3-dihydro-indol-2-one

A solution of 5-methylisatin (15.0 g) and hydrazine hydrate (60 mL) was heated to 140–160° C. for 4 hours. The reaction mixture was cooled to room temperature, poured into 300 mL of ice water and acidified to pH 2 with 6 N hydrochloric acid. After standing at room temperature for 2 days the precipitate was collected by vacuum filtration, washed with water and dried under vacuum to give 6.5 g (47% yield) of 5-methyl-2-oxindole.

$^1$H NMR (360 MHz, DMSO-$d_6$) δ10.20 (s, br, 1H, NH), 6.99 (s, 1H, H-4), 6.94 (d, J=8 Hz, 1H, H-6), 6.68 (d, J=8 Hz, 1H, H-7), 3.39 (s, 2H, $CH_2$-3) and 2.22 (s, 3H, $CH_3$-5).

3-Methylindole-2-carbaldehyde was prepared as described in the literature: 1) David W. M. Benzies, Pilar Matinez Fresneda and R. Alan Jones, *Synthetic Communications*, 16 (14), 1799–1807 (1986) and 2) Chatterjee, A. and Biswas, K. M., *J. Org. Chem.*, 1973, 38,4002.

A mixture of 5-methyl-2-oxindole (59 mg), 3-methylindole-2-carbaldehyde (56 mg) and piperidine (30 mg) in ethanol (1 mL) was heated in a sealed tube at 90° C. for overnight. The mixture was cooled to room temperature. The solid was collected by vacuum filtration, washed with cold ethanol and dried in a vacuum oven for overnight to give 72 mg (74% yield) of 5-methyl-3-(3-methyl-1H-indol-2-ylmethylene)-1,3-dihydro-indol-2-one.

$^1$H NMR (360 MHz, DMSO-$d_6$) 13.03 (s, br, 1H, NH), 10.88 (s, br, 1H, NH), 7.84 (s, 1H, vinyl), 7.71 (s, br, 1H), 6.62 (d, J=8 Hz, 1H), 7.48 (d, J=8 Hz, 1H), 7.26 (t, J=7 Hz, 1H), 7.06 (t, J=7 Hz, 1H), 7.0 (d, J=8 Hz, 1H), 6.78 (d, J=8 Hz, 1H), 2.59 (s, 3H, CH$_3$), 2.32 (s, 3H, CH$_3$). MS m/z 289 [M+1]$^+$.

Compound IN-002

3-(3-Methyl-1H-indol-2-ylmethylene)-2-oxo-2,3-dihydro-1H-indole-5-sulfonic acid amide To a 100 mL flask charged with 27 mL of chlorosulfonic acid was added slowly 13.3 g of 2-oxindole. The reaction temperature was maintained below 30° C. during the addition. After the addition, the reaction mixture was stirred at room temperature for 1.5 hours, heated to 68° C. for 1 hour, cooled, and poured into water. The precipitate was washed with water and dried.

To a 100 mL flask charged with 27 mL of chlorosulfonic acid was added slowly 13.3 g of 2-oxindole. The reaction temperature was maintained below 30° C. during the addition. After the addition, the reaction mixture was stirred at room temperature for 1.5 hours, heated to 68° C. for 1 hour, cooled, and poured into water. The precipitate was washed with water and dried in a vacuum oven to give 11.0 g of 5-chlorosulfonyl-2-oxindole (50% yield) which was used without further purification.

5-Chlorosulfonyl-2-oxindole (2.1 g) was added to 10 mL of ammonium hydroxide in 10 mL of ethanol and stirred at room temperature overnight. The mixture was concentrated and the solid collected by vacuum filtration to give 0.4 g (20% yield) of 5-aminosulfonyl-2-oxindole as an off-white solid.

$^1$H NMR (360 MHz, DMSO-d$_6$) δ10.67 (s, 1H, NH-1), 7.63–7.66 (m, 2H, H-4,6), 7.13 (s, 2H, 5-SO$_2$NH$_2$), 6.91 (d, J=8 Hz, 1H, H-7), and 3.56 (s, 2H, CH$_2$-3). MS m/z 211 [M–1]$^+$.

A mixture of 5-aminosulfonyl-2-oxindole (84 mg), 3-methylindole-2-carbaldehyde (56 mg) (prepared according to *Synthetic Communications*, 1986, 16, 1799) and piperidine (30 mg) in ethanol (1 mL) was heated in a sealed tube at 90° C. for overnight. The mixture was cooled to room temperature. The solid was collected by vacuum filtration, washed with cold ethanol and dried in oven for overnight to give 88 mg (71% yield) of 3-(3-methyl-1H-indol-2-ylmethylene)-2-oxo-2,3-dihydro-1H-indole-5-sulfonic acid amide.

$^1$H NMR (360 MHz, DMSO-d$_6$) 12.86 (s, br, 1H, NH), 11.3 (s, br, 1H, NH), 8.3 (d, J=2 Hz, 1H), 7.97 (s, 1H, vinyl), 7.63 (dd, J=2 and 8 Hz, 1H), 7.6 (d, J=8 Hz, 1H), 7.47 (d, J=8 Hz, 1H), 7.24 (t, J=7.5 Hz, 1H), 7.12 (s, br, 2H, NH$_2$), 7.02 (t, J=7.5 Hz, 1H), 6.98 (d, J=8 Hz, 1H), 2.57 (s, 3H, CH$_3$). MS m/z 354.1 [M+1]$^+$ Compound IN-003

3-(3-Methyl-1H-indol-2-ylmethylene)-2-oxo-2,3-dihydro-1H-indole-5-sulfonic acid methylamide A suspension of 5-chlorosulfonyl-2-oxindole (3.38 g) (prepared as described in Compound IN-02) in 2 M methylamine in tetrahydrofuran (10 mL) was stirred at room temperature for 4 hours at which time a white solid was present. The precipitate was collected by vacuum filtration, washed twice with 5 mL of water each time and dried under vacuum at 40° C. overnight to give 3.0 g (88% yield) of 5-methylaminosulfonyl-2-oxindole.

$^1$H NMR (300 MHz, DMSO-d$_6$) δ10.87 (s, br, 1H, NH-1), 7.86 (s, br, 1H, 5-SO$_2$NHCH$_3$), 7.61 (d, J=8 Hz 1H, H-6), 7.32 (d, J=5 Hz, 1H, H-4), 6.97 (d, J=8 Hz, 1H, H-7), 2.53 (s, 2H, CH$_2$-3), and 2.36 (s, 3H, 5-SO$_2$NHCH$_3$). MS m/z 226.

A mixture of 5-methylaminosulfonyl-2-oxindole (90 mg), 3-methylindole-2-carbaldehyde (56 mg) (prepared according to *Synthetic Communications*, 1986, 16, 1799) and piperidine (30 mg) in ethanol (1 mL) was heated in a sealed tube at 90° C. for overnight. The mixture was cooled to room temperature. The solid was collected by vacuum filtration, washed with cold ethanol and dried in oven for overnight to give 90 mg (70% yield) of 3-(3-methyl-1H-indol-2-ylmethylene)-2-oxo-2,3-dihydro-1H-indole-5-sulfonic acid methylamide (mixture of isomers).

$^1$H NMR (360 MHz, DMSO-d$_6$) 11.13 (s, br, 1H, NH), 10.94 (s, br, 1H, NH), 8.84 (d, J=16 Hz, 1H), 7.98 (s, 1H), 6.97–7.66 (m, 6H, Ar—H), 2.6 (s, 3H, CH$_3$), 2.4 (d, J=5 Hz, 3H, CH$_3$N.

Compound IN-004

3-(3-Methyl-1H-indol-2-ylmethylene)-2-oxo-2,3-dihydro-1H-indole-5-sulfonic acid dimethylamide A suspension of 2.3 g of 5-chlorosulfonyl-2-oxindole (prepared as described in Compound IN-02) in 10 mL of 2 M dimethylamine in methanol was stirred at room temperature for 4 hours at which time a white solid was present. The precipitate was collected by vacuum filtration, washed with 5 mL of 1 N sodium hydroxide and 5 mL of 1 N hydrochloric acid and dried under vacuum at 40° C. overnight to give 1.9 g (79% yield) of 5-dimethylaminosulfonyl-2-oxindole.

$^1$H NMR (300 MHz, DMSO-d$_6$) δ10.87 (s, br, 1H, NH), 7.73 (d, J=1 Hz, 1H, H-4), 7.58 (dd, J=1, 8 Hz, 1H, H-6), 7.02 (d, J=8 Hz, 1H, H-7), 2.59 (s, 3H, CH$_3$) 2.54 (s, 2H, H-3), 2.36 (s, 3H, CH$_3$).

A mixture of 5-dimethylaminosulfonyl-2-oxindole (96 mg), 3-methylindole-2-carbaldehyde (56 mg) (prepared according to *Synthetic Communications*, 1986, 16, 1799) and piperidine (30 mg) in ethanol (1 mL) was heated in a sealed tube at 90° C. for overnight. The mixture was cooled to room temperature. The solid was collected by vacuum filtration, washed with cold ethanol and dried in oven for overnight to give 76 mg (57% yield) of 3-(3-methyl-1H-indol-2-ylmethylene)-2-oxo-2,3-dihydro-1H-indole-5-sulfonic acid dimethylamide (mixture of isomers).

$^1$H NMR (360 MHz, DMSO-d$_6$) 11.09 (s, br, 1H, NH), 10.95 (s, br, 1H, NH), 8.78 (d, J=16 Hz, 1H), 7.8 (s, 1H, vinyl), 7.45–7.54 (m, 2H), 7.32 (d, J=8 Hz, 1H), 7.1 (t, 1H), 6.98 (d, J=8 Hz, 1H), 6.93 (t, 1H), 2.56 (s, 6H, 233 CH$_3$), 2.39 (s, 3H, CH$_3$)

Compound IN-005

3-(3-Methyl-1H-indol-2-ylmethylene)-2-oxo-2,3-dihydro-1H-indole-5-carboxylic acid (piperidine salt)

2-Oxindole (6.7 g) was added to a stirred suspension of 23 g of aluminum chloride in 30 mL of dichloroethane in an ice bath. Chloroacetyl chloride (11.3 g) was slowly added and hydrogen chloride gas was evolved. After ten minutes of stirring, the reaction was warmed to 40–50° C. for 1.5 hours. The mixture was cooled to room temperature and poured into ice water. The precipitate was collected by vacuum filtration, washed with water and dried under vacuum to give 10.3 g (98%) of 5-chloroacetyl-2-oxindole as an off-white solid.

A suspension of 9.3 g of 5-chloroacetyl-2-oxindole was stirred in 90 mL of pyridine at 80–90° C. for 3 hours then cooled to room temperature. The precipitate was collected by vacuum filtration and washed with 20 mL of ethanol. The solid was dissolved in 90 mL of 2.5 N sodium hydroxide and stirred at 70–80° C. for 3 hours. The mixture was cooled to room temperature and acidified to pH 2 with 0.5 N hydrochloric acid. The precipitate was collected by vacuum filtration and washed thoroughly with water to give crude 5-carboxy-2-oxindole as a dark brown solid. After standing overnight the filtrate yielded 2 g of 5-carboxy-2-oxindole as a yellow solid. The crude dark brown product was dissolved in hot methanol, the insoluble material removed by filtration and the filtrate concentrated to give 5.6 g of 5-carboxy-2-oxindole as a brown solid. The combined yield was 97%.

$^1$H NMR (360 MHz, DMSO-d$_6$) δ12.56 (s, br, 1H, COOH-5), 10.70 (s, 1H, NH-1), 7.82 (dd, J=2, 8 Hz, 1H, H-6), 7.74 (s, br, 1H, H-4), 6.87 (d, J=8 Hz, 1H, H-7), and 3.53 (s, 2H, CH$_2$-3). MS m/z 178 [M+1]$^+$.

A mixture of 5-carboxy-2-oxindole (113 mg), 3-methylindole-2-carbaldehyde (56 mg) (prepared according to *Synthetic Communications*, 1986, 16, 1799) and piperidine (30 mg) in ethanol (1 mL) was heated in a sealed tube at 90° C. for overnight. The mixture was cooled to room temperature. The solid was collected by vacuum filtration, washed with cold ethanol and dried in oven for overnight to give 75 mg (58% yield) of 3-(3-methyl-1H-indol-2-ylmethylene)-2-oxo-2,3-dihydro-1H-indole-5-carboxylic acid (piperidine salt).

$^1$H NMR (360 MHz, DMSO-d$_6$) 13.0 (s, br, 1H, NH), 8.35 (d, J=1.5 Hz, 1H, H-4), 7.91 (s, 1H, vinyl), 7.82 (dd, J=1.5 and 8 Hz, 1H, H-6), 7.63 (d, J=8 Hz, 1H), 7.49 (d, J=8 Hz, 1H), 7.26 (t, J=7.5 Hz, 1H), 7.06 (t, J=7.5 Hz, 1H), 6.8 (d, J=8 Hz, 1H), 2.91 (t, 4H, piperidine), 2.6 (s, 3H, CH$_3$), 1.6 (m, 4H, piperidine), 1.54 (m, 2H, piperidine).
Compound IN-006

5-Acetyl-3-(3-methyl-1H-indol-2-ylmethylene)-1,3-dihydro-indol-2-one

2-Oxindole (3 g) was suspended in 1,2-dichloroethane and slowly treated with 3.2 mL of acetyl chloride. The resulting suspension was heated to 50° C. for 5 hours, cooled, and poured into water. The resulting precipitate was collected by vacuum filtration, washed copiously with water and dried under vacuum to give 2.9 g (73% yield) of 5-acetyl-2-oxindole as a brown solid.

$^1$H NMR (360 MHz, DMSO-d$_6$) δ10.75 (s, br, NH), 7.83 (d, J=8 Hz, 1H), 7.78 (s, 1H, H-4), 6.88 (d, J=8 Hz, 1H), 3.53 (s, 2H, CH$_2$), 2.49 (s, 3H, CH$_3$).

A mixture of 5-acetyl-2-oxindole (70 mg), 3-methylindole-2-carbaldehyde (56 mg) (prepared according to *Synthetic Communications*, 1986, 16, 1799) and piperidine (30 mg) in ethanol (1 mL) was heated in a sealed tube at 90° C. for overnight. The mixture was cooled to room temperature. The solid was collected by vacuum filtration, washed with cold ethanol and dried in oven for overnight to give 83 mg (75% yield) of 5-acetyl-3-(3-methyl-1H-indol-2-ylmethylene)-1,3-dihydro-indol-2-one.

$^1$H NMR (360 MHz, DMSO-d$_6$) 12.86 (s, br, 1H, NH), 11.29 (s, br, 1H, NH), 8.43 (d, J=1.5 Hz, 1H, H-4), 8.01 (s, 1H, vinyl), 7.78 (dd, J=1.5 and 8 Hz, 1H, H-6), 7.58 (d, J=8 Hz, 1H), 7.45 (d, J=8 Hz, 1H), 7.23 (t, 1H), 7.01 (t, 1H), 6.92 (d, J=8 Hz, 1H), 2.58 (s, 3H, CH$_3$), 2.54 (s, 3H, CH$_3$). MS m/z 317.2 [M+1]$^+$.
Compound IN-007

5-Acetyl-3-(1H-indol-2-ylmethylene)-1,3-dihydro-indol-2-one

Indole-2-carbaldehyde was prepared as described in the literature: Michel Barbier, Michel Devys, Christiane Tempête, Albert Kollmann and Jean-Francois Bousquet, *Synthetic Communications*, 23(22), 3109–3117 (1993).

A mixture of 5-acetyl-2-oxindole (88 mg) (prepared as described in Compound IN-06), indole-2-carbaldehyde (87 mg) and piperidine (4 mg) in ethanol (2 mL) was heated in a sealed tube at 90° C. for 3 hours. The mixture was cooled to room temperature. The solid was collected by vacuum filtration, washed with cold ethanol and dried in oven for overnight to give 133 mg (88% yield) of 5-acetyl-3-(1H-indol-2-ylmethylene)-1,3-dihydro-indol-2-one as an orange solid.

$^1$H NMR (360 MHz, DMSO-d$_6$) 12.81 (s, br, 1H, NH), 11.38 (s, br, 1H, NH), 8.38 (d, J=1 Hz, H-4), 8.17 (s, 1H, vinyl), 7.88 (dd, J=1 and 8 Hz, 1H, H-6), 7.69 (d, J=8 Hz, 1H), 7.58 (d, J=8 Hz, 1H), 7.29 (t, 1H), 7.21 (s, 1H), 7.09 (t, 1H), 7.0 (d, J=8 Hz, 1H), 2.59 (s, 3H, CH$_3$). MS m/z 303.1 [M+1]$^+$.
Compound IN-008

3-(1H-Indol-2-ylmethylene)-2-oxo-2,3-dihydro-1H-indole-5-sulfonic acid amide A mixture of 5-aminosulfonyl-2-oxindole (106 mg) (prepared as described in Compound IN-02), indole-2-carbaldehyde (87 mg) (prepared according to *Synthetic Communications*, 1993, 23, 3109) and piperidine (4 mg) in ethanol (2 mL) was heated in a sealed tube at 90° C. for 3 hours. The mixture was cooled to room temperature. The solid was collected by vacuum filtration, washed with cold ethanol and dried in oven for overnight to give 140 mg (83% yield) of 3-(1H-indol-2-ylmethylene)-2-oxo-2,3-dihydro-1H-indole-5-sulfonic acid amide as an orange solid.

$^1$H NMR (360 MHz, DMSO-d$_6$) 12.81 (s, br, 1H, NH), 11.38 (s, br, 1H, NH), 8.18 (d, J=1 Hz, H-4), 8.12 (s, 1H, vinyl), 7.7 (m, 2H), 7.6 (d, J=8 Hz, 1H), 7.26–7.29 (m, 2H), 7.2 (s, 2H, NH$_2$), 7.05–7.11 (m, 2H). MS m/z 340 [M+1]$^+$.
Compound IN-009

5-Amino-3-(1H-indol-2-ylmethylene)-1,3-dihydro-indol-2-one

2-Oxindole (6.5 g) was dissolved in 25 mL of concentrated sulfuric acid and the mixture maintained at −10–15° C. while 2.1 mL of fuming nitric acid was added dropwise. After the addition of the nitric acid the reaction mixture was stirred at 0° C. for 0.5 hour and poured into ice-water. The precipitate was collected by filtration, washed with water and crystallized from 50% acetic acid. The final crystalline product was then filtered, washed with water and dried under vacuum to give 6.3 g (70%) of 5-nitro-2-oxindole.

5-Nitro-2-oxindole (6.3 g) was hydrogenated in methanol over 10% palladium on carbon to give 3.0 g (60% yield) of 5-amino-2-oxindole as a white solid.

A mixture of 5-amino-2-oxindole (1.8 g) and di-tert-butyl dicarbonate (3.27 g) in butanol (20 mL) was stirred at 100° C. for one hour. The reaction mixture was cooled to room temperature and poured into ice-water. The precipitate was collected by vacuum filtration, washed with water and dried in vacuum oven for overnight to give 2.75 g (92% yield) of 5-tert-butoxycarbonylamino-2-oxindole as a white solid.

A mixture of 5-tert-butoxycarbonylamino-2-oxindole (124 mg), indole-2-carbaldehyde (87 mg) (prepared according to *Synthetic Communications*, 1993, 23, 3109) and piperidine (4 mg) in ethanol (2 mL was heated in a sealed tube at 90° C. for 3 hours. The mixture was cooled to room temperature. The solid was collected by vacuum filtration, washed with cold ethanol and dried in oven for overnight to give 196 mg of 5-tert-butoxycarbonylamino-3-(1H-indol-2-ylmethylene)-1,3-dihydro-indol-2-one as a bright orange solid. It was then dissolved in trifluoroacetic acid/dichloromethane mixture (2 mL each) and stirred at room temperature for 1 hour. The reaction mixture was concentrated. The residue was dissolved in water and basified with saturated sodium bicarbonate solution. The solid was collected by vacuum filtration, washed with water and dried in vacuum oven for overnight to give 129 mg of 5-amino-3-(1H-indol-2-ylmethylene)-1,3-dihydro-indol-2-one as a brown solid.

$^1$H NMR (360 MHz, DMSO-$d_6$) 13.1 (s, br, 1H, NH), 10.57 (s, br, 1H, NH), 7.65 (s, 1H, vinyl), 7.64 (d, J=8 Hz, 1H), 7.54 (d, J=8 Hz, 1H), 7.24 (t, 1H), 7.1 (s, 1H), 7.06 (t, 1H), 6.93 (d, J=2 Hz, 1H), 6.61 (d, J=8 Hz, 1H), 6.5 (dd, J=2 and Hz, 1H), 4.8 (s, br, 2H, NH$_2$). MS m/z 276.1 [M+1]$^+$.
Compound IN-010

3-(1H-Indol-2-ylmethylene)-2-oxo-2,3-dihydro-1H-indole-5-carboxylic acid

A mixture of 5-carboxy-2-oxindole (88.5 mg) (prepared as described in Compound IN-05), indole-2-carbaldehyde (87 mg) (prepared according to *Synthetic Communications,* 1993, 23, 3109) and piperidine (1 drop) in ethanol (3 mL) was heated in a sealed tube at 95° C. for 4 hours. The mixture was cooled to room temperature. The solid was filtered and acidified with 2N hydrochloric acid. The resulting darker solid was collected by vacuum filtration, washed with cold ethanol and dried in vacuum oven for overnight to give 60 mg (40% yield) of 3-(1H-indol-2-ylmethylene)-2-oxo-2,3-dihydro-1H-indole-5-carboxylic acid as a mustard-colored solid.

$^1$H NMR (360 MHz, DMSO-$d_6$) 12.8 (s, br, 1H, NH), 12.69 (s, 1H, COOH), 11.35 (s, br, 1H, NH), 8.33 (s, 1H), 8.16 (s, 1H), 7.86 (dd, J=1 and 8 Hz, 1H), 7.68 (d, J=8 Hz, 1H), 7.59 (d, J=8 Hz, 1H), 7.28 (t, 1H), 7.21 (s, 1H), 7.08 (t, 1H), 6.99 (d, J=8 Hz, 1H). MS m/z 304 [M]$^+$.
Compound IN-011

6-Chloro-3-(1H-indol-2-ylmethylene)-1,3-dihydro-indol-2-one

A mixture of 6-chloro-2-oxindole (41 mg) (commercially available), indole-2-carbaldehyde (42 mg) (prepared according to *Synthetic Communications,* 1993, 23, 3109) and piperidine (1 drop) in ethanol (3 mL) was heated in a sealed tube at 95° C. for 3 hours. The mixture was cooled to room temperature. The solid was collected by vacuum filtration, washed with cold ethanol and dried in vacuum oven for overnight to give 62 mg (87% yield) of 6-chloro-3-(1H-indol-2-ylmethylene)-1,3-dihydro-indol-2-one as a shiny orange solid.

$^1$H NMR (360 MHz, DMSO-$d_6$) 12.83 (s, br, 1 H, NH), 11.17 (s, br, 1H, NH), 7.98 (s, 1H), 7.74 (d, J=8 Hz, 1H), 7.67 (d, J=8 Hz, 1H), 7.58 (d, J=8 Hz, 1H), 7.28 (m, 1H), 7.15 (s, br, 1H), 7.08 (m, 2H), 6.91 (d, J=2 Hz, 1H). MS m/z 293 and 295.
Compound IN-012

3-(1H-Indol-2-ylmethylene)-1,3-dihydro-indol-2-one

A mixture of 2-oxindole (133 mg), indole-2-carbaldehyde (174 mg) (prepared according to *Synthetic Communications,* 1993, 23, 3109) and piperidine (10 mg) in ethanol was heated in a sealed tube at 95° C. for 4 hours. The mixture was cooled to room temperature. The solid was collected by vacuum filtration, washed with cold ethanol and dried in vacuum oven for overnight to give 3-(1H-indol-2-ylmethylene)-1,3-dihydro-indol-2-one.

$^1$H NMR (360 MHz, DMSO-$d_6$) δ12.97 (s, br, 1H, NH), 11.01 (s, br, 1H, NH), 7.92 (s, 1H, H-vinyl), 7.72 (d, J=7 Hz, 1H), 7.66 (d, J=7 Hz, 1H), 7.57 (dd, J=1, 8 Hz, 1H), 7.27 (dt, J=1, 7 Hz, 1H), 7.21 (dt, J=1, 8 Hz, 1H), 7.13 (s, 1H), 7.01–7.1 (m, 2H), 6.91 (d, J=8 Hz, 1H). MS EI 260.
Compound IN-013

5—Chloro-3-(1H-indol-2-ylmethylene)-1,3-dihydro-indol-2-one

A mixture of 5-chloro-2-oxindole (167 mg), indole-2-carbaldehyde (174 mg) (prepared according to *Synthetic Communications,* 1993, 23, 3109) and piperidine (10 mg) in ethanol was heated in a sealed tube at 95° C. for 4 hours. The mixture was cooled to room temperature. The solid was collected by vacuum filtration, washed with cold ethanol and dried in vacuum oven for overnight to give 5-chloro-3-(1H-indol-2-ylmethylene)-1,3-dihydro-indol-2-one.

$^1$H NMR (360 MHz, DMSO-$d_6$) δ12.88 (s, br, 1H, NH), 11.12 (s, br, 1H, NH), 8.07 (s, 1H, H-vinyl), 7.86 (d, J=2 Hz, 1H), 7.68 (d, J=8 Hz, 1H), 7.59 (dd, J=1, 8 Hz, 1H), 7.28 (m, 1H), 7.24 (dd, J=2, 8 Hz, 1H), 7.14 (s, 1H), 7.09 (dt, J=1, 8 Hz, 1H), 6.90 (d, J=8 Hz, 1H). MS EI 294 and 296.
Compound IN-014

5-Bromo-3-(1H-indol-2-ylmethylene)-1,3-dihydro-indol-2-one

2-Oxindole (1.3 g) in 20 mL of acetonitrile was cooled to −10° C. and 2.0 g of N-bromosuccinimide was slowly added with stirring. The reaction was stirred for 1 hour at −10° C. and 2 hours at 0° C. The precipitate was collected, washed with water and dried to give 1.9 g (90% yield) of 5-bromo-2-oxindole.

$^1$H NMR (360 MHz, DMSO-$d_6$) δ10.44 (s, br, 1H, NH-1), 7.32–7.36 (m, 2H), 6.76 (d, J=8.5 Hz, 1H, H-7), 3.5 (s, 2H, CH$_2$). MS m/z 212.1 and 214.1 [M and M+2]$^+$.

A mixture of 5-bromo-2-oxindole (212 mg), indole-2-carbaldehyde (174 mg) (prepared according to *Synthetic Communications,* 1993, 23, 3109) and piperidine (10 mg) in ethanol was heated in a sealed tube at 95° C. for 4 hours. The mixture was cooled to room temperature. The solid was collected by vacuum filtration, washed with cold ethanol and dried in vacuum oven for overnight to give 5-bromo-3-(1H-indol-2-ylmethylene)-1,3-dihydro-indol-2-one.

$^1$H NMR (360 MHz, DMSO-$d_6$) δ12.87 (s, br, 1H, NH), 11.12 (s, br, 1H, NH), 8.07 (s, 1H, H-vinyl), 7.98 (d, J=2 Hz, 1H), 7.68 (d, J=8 Hz, 1H), 7.59 (d, J=8 Hz, 1H), 7.36 (dd, J=2, 8 Hz, 1H), 7.28 (dt, J=1, 8 Hz, 1H), 7.14 (s, 1H), 7.08 (dt, J=1, 8 Hz, 1H), 6.86 (d, J=8 Hz, 1H). MS EI 338 and 340.
Compound IN-015

3-(1H-indol-2-ylmethylene)-4-methyl-1,3-dihydro-indol-2-one

Diethyl oxalate (30 mL) in 20 mL of dry ether was added with stirring to 19 g of potassium ethoxide suspended in 50 mL of dry ether. The mixture was cooled in an ice bath and 20 mL of 3-nitro-o-xylene in 20 mL of dry ether was slowly added. The thick dark red mixture was heated to reflux for 0.5 hour, concentrated to a dark red solid, and treated with 10% sodium hydroxide until almost all of the solid dissolved. The dark red mixture was treated with 30% hydrogen peroxide until the red color changed to yellow. The mixture was treated alternately with 10% sodium hydroxide and 30% hydrogen peroxide until the dark red color was no longer present. The solid was filtered off and the filtrate acidified with 6 N hydrochloric acid. The resulting precipitate was collected by vacuum filtration, washed with water, and dried under vacuum to give 9.8 g (45% yield) of 1-methyl-6-nitrophenylacetic acid as an off-white solid. The solid was hydrogenated in methanol over 10% palladium on carbon to give 9.04 g of 4-methyl-2-oxindole as a white solid.

$^1$H NMR (360 MHz, DMSO-d$_6$) δ10.27 (s, br, 1H, NH), 7.06 (t, J=8 Hz, 1H, H-6), 6.74 (d, J=8 Hz, H-5), 6.63 (d, J=8 Hz, 1H, H-7), 3.36 (s, 2H, CH$_2$), 2.18 (s, 3H, CH$_3$).

A mixture of 4-methyl-2-oxindole (147 mg), indole-2-carbaldehyde (174 mg) (prepared according to *Synthetic Communications*, 1993, 23, 3109) and piperidine (10 mg) in ethanol was heated in a sealed tube at 95° C. for 4 hours. The mixture was cooled to room temperature. The solid was collected by vacuum filtration, washed with cold ethanol and dried in vacuum oven for overnight to give 3-(1H-indol-2-ylmethylene)-4-methyl-1,3-dihydro-indol-2-one.

$^1$H NMR (360 MHz, DMSO-d$_6$) δ13.12 (s, br, 1H, NH), 11.02 (s, br, 1H, NH), 7.79 (s, 1H, H-vinyl), 7.64 (d, J=8 Hz, 1H), 7.57 (d, J=8 Hz, 1H), 7.27 (d, J=7 Hz, 1H), 7.23 (s, 1H), 7.05–7.14 (m, 2H), 6.84 (d, J=8 Hz, 1H), 6.78 (d, J=8 Hz, 1H), 2.61 (s, 3H, CH$_3$). MS El 274.

Compound IN-016

3-(3-Methyl-1H-indol-2-ylmethylene)-1,3-dihydro-indol-2-one

A mixture of 2-oxindole (133 mg), 3-methyl-indole-2-carbaldehyde (190 mg) (prepared according to *Synthetic Communications*, 1986, 16, 1799) and piperidine (10 mg) in ethanol was heated in a sealed tube at 95° C. for 4 hours. The mixture was cooled to room temperature. The solid was collected by vacuum filtration, washed with cold ethanol and dried in vacuum oven for overnight to give 3-(3-methyl-1H-indol-2-ylmethylene)-1,3-dihydro-indol-2-one.

$^1$H NMR (360 MHz, DMSO-d$_6$) δ13.01 (s, br, 1H, NH), 10.99 (s, br, 1H, NH), 7.89 (s, 1H, H-vinyl), 7.88 (d, J=7 Hz, 1H), 7.63 (d, J=8 Hz, 1H), 7.49 (d, J=8 Hz, 1H), 7.27 (dt, J=1, 8 Hz, 1H), 7.2 (dt, J=1, 8 Hz, 1H), 7.01–7.08 (m, 2H), 6.9 (d, J=8 Hz, 1H), 2.59 (s, 3H, CH$_3$). MS El 274.

Compound IN-017

5-Chloro-3-(3-methyl-1H-indol-2-ylmethylene)-1,3-dihydro-indol-2-one

A mixture of 5-chloro-2-oxindole (167 mg), 3-methyl-indole-2-carbaldehyde (190 mg) (prepared according to *Synthetic Communications*, 1986, 16, 1799) and piperidine (10 mg) in ethanol was heated in a sealed tube at 95° C. for 4 hours. The mixture was cooled to room temperature. The solid was collected by vacuum filtration, washed with cold ethanol and dried in vacuum oven for overnight to give 5-chloro-3-(3-methyl-1H-indol-2-ylmethylene)-1,3-dihydro-indol-2-one.

$^1$H NMR (360 MHz, DMSO-d$_6$) δ12.96 (s, br, 1H, NH), 11.09 (s, br, 1H, NH), 8.09 (d, J=2 Hz, 1H), 8.02 (s, 1H, H-vinyl), 7.63 (d, J=8 Hz, 1H), 7.5 (d, J=8 Hz, 1H), 7.29 (dt, J=1, 7 Hz, 1H), 7.21 (dd, J=2, 8 Hz, 1H), 7.07 (dt, J=1, 7 Hz, 1H), 6.89 (d, J=8 Hz, 1H), 2.61 (s, 3H, CH$_3$). MS El 308.

Compound IN-018

5-Bromo-3-(3-methyl-1H-indol-2-ylmethylene)-1,3-dihydro-indol-2-one

A mixture of 5-bromo-2-oxindole (212 mg) (prepared as described in Compound IN-014), 3-methyl-indole-2-carbaldehyde (190 mg) (prepared according to *Synthetic Communications*, 1986, 16, 1799) and piperidine (10 mg) in ethanol was heated in a sealed tube at 95° C. for 4 hours. The mixture was cooled to room temperature. The solid was collected by vacuum filtration, washed with cold ethanol and dried in vacuum oven for overnight to give 5-bromo-3-(3-methyl-1H-indol-2-ylmethylene)-1,3-dihydro-indol-2-one.

$^1$H NMR (360 MHz, DMSO-d$_6$) δ12.96 (s, br, 1H, NH), 11.09 (s, br, 1H, NH), 8.21 (d, J=2 Hz, 1H), 8.02 (s, 1H, H-vinyl), 7.63 (d, J=8 Hz, 1H), 7.5 (d, J=8 Hz, 1H), 7.33 (dd, J=2, 8 Hz, 1H), 7.29 (dt, J=1, 7 Hz, 1H), 7.07 (dt, J=1, 7 Hz, 1H), 6.84 (d, J=8 Hz, 1H), 2.62 (s, 3H, CH$_3$). MS El 352 and 354.

Compound IN-019

4-Methyl-3-(3-methyl-1H-indol-2-ylmethylene)-1,3-dihydro-indol-2-one

A mixture of 4-methyl-2-oxindole (147 mg) (prepared as described in Compound IN-015), 3-methyl-indole-2-carbaldehyde (190 mg) (prepared according to *Synthetic Communications*, 1986, 16, 1799) and piperidine (10 mg) in ethanol was heated in a sealed tube at 95° C. for 4 hours. The mixture was cooled to room temperature. The solid was collected by vacuum filtration, washed with cold ethanol and dried in vacuum oven for overnight to give 4-methyl-3-(3-methyl-1H-indol-2-ylmethylene)-1,3-dihydro-indol-2-one.

$^1$H NMR (360 MHz, DMSO-d$_6$) δ13.07 (s, br, 1H, NH), 11.0 (s, br, 1H, NH), 7.78 (s, 1H, H-vinyl), 7.64 (d, J=8 Hz, 1H), 7.51 (d, J=8 Hz, 1H), 7.27 (dt, J=1, 8 Hz, 1H), 7.04–7.12 (m, 2H), 6.85 (d, J=8 Hz, 1H), 6.78 (d, J=8 Hz, 1H), 2.64 (s, 3H, CH$_3$), 2.52 (s, 3H, CH$_3$). MS El 288.

Compound IN-020

3-(1H-indol-2-ylmethylene)-5-[(1H-indol-2-ylmethylene)-amino]-1,3-dihydro-indol-2-one A mixture of 5-amino-2-oxindole (74 mg) (prepared as described in Compound IN-009), indole-2-carbaldehyde (87 mg) (prepared according to *Synthetic Communications*, 1983, 23, 3109) and piperidine (4 mg) in ethanol (2 mL) was heated in a sealed tube at 95° C. for 3 hours. The mixture was cooled to room temperature. The solid was collected by vacuum filtration, washed with cold ethanol and dried in vacuum oven for overnight. The crude solid was then chromatographed on a column of silica gel to give 50 mg (25% yield) of 3-(1H-indol-2-ylmethylene)-5-[(1H-indol-2-ylmethylene)-amino]-1,3-dihydro-indol-2-one Example 2

Assay Measuring the Kinase Activity of the FLK-1 Receptor

An ELISA assay was conducted to measure the kinase activity of the FLK-1 receptor and more specifically, the inhibition or activation of TK activity on the FLK-1 receptor. Specifically, the following assay was conducted to measure kinase activity of the FLK-1 receptor in cells genetically engineered to express FLK-1.

Materials and Methods

Materials

The following reagents and supplies were used:
(1) Corning 96-well ELISA planes (Corning Catalog No. 25805-96);
(2) Cappel goat anti-rabbit IgG (catalog no. 55641);
(3) PBS (Gibco Catalog No. 450-1300EB);
(4) TBSW Buffer (50 mM Tris pH 7.2), 150 mM NaCl and 0.1% Tween-20);

(5) Ethanolamine stock (10% ethanolamine (pH 7.0), stored at 4° C.);
(6) HNTG buffer (20 mM HEPES buffer (pH 7.5), 150 mM NaCl, 0.2% Triton X-100, and glycerol);
(7) EDTA (0.5 M (pH 7.0) as a 100×stock);
(8) Sodium ortho vanadate (0.5 M as a 100×stock);
(9) Sodium pyro phosphate (0.2 M as a 100×stock);
(10) NUNC 96 well V bottom polypropylene plates (Applied Scientific Catalog No. AS-72092);
(11) NIH3T3 C7#3 Cells (FLK-1 expressing cells);
(12) DMEM with 1×high glucose L Glutamine (catalog No. 11965-050);
(13) FBS, Gibco (catalog no. 16000-028);
(14) L-glutamine, Gibco (catalog no. 25030-016);
(15) VEGF, PeproTech, Inc. (catalog no. 100-20)(kept as 1 $\mu$g/100 $\mu$L stock in Milli-Q $dH_2O$ and stored at −20° C.;
(16) Affinity purified anti-FLK-1 antiserum;
(17) UB40 monoclonal antibody specific for phosphotyrosine (see, Fendley, et al., 1990, *Cancer Research* 50:1550–1558);
(18) EIA grade Goat anti-mouse IgG-POD (BioRad catalog no. 172-1011);
(19) 2,2-azino-bis(3-ethylbenz-thiazoline-6-sulfonic acid (ABTS) solution (100 mM citric acid (anhydrous), 250 mM $Na_2HPO_4$ (pH 4.0), 0.5 mg/mL ABTS (Sigma catalog no. A-1888)), solution should be stored in dark at 4° C. until ready for use;
(20) $H_2O_2$ (30% solution) (Fisher catalog no. H325);
(21) $ABTS/H_2O_2$ (15 mL ABTS solution,2 $\mu$L $H_2O_2$) prepared 5 minutes before use and left at room temperature;
(22) 0.2 M HCl stock in $H_2O$;
(23) dimethylsulfoxide (100%) (Sigma Catalog No. D-8418); and
(24) Trypsin-EDTA (Gibco BRL Catalog No.25200-049).

Protocol

The following protocol was used for conducting the assay:
1. Coat Corning 96-well elisa plates with 1.0 $\mu$g per well Cappel Anti-rabbit IgG antibody in 0.1 M $Na_2CO_3$ pH 9.6. Bring final volume to 150 $\mu$L per well. Coat plates overnight at 4° C. Plates can be kept up to two weeks when stored at 4° C.
2. Grow cells in Growth media (DMEM, supplemental with 2.0 mM L-Glutamine, 10% FBS) in suitable culture dishes until confluent at 37° C., 5% $CO_2$.
3. Harvest cells by trypsinization and seed in Corning 25850 polystyrene 96-well roundbottom cell plates, 25.000 cells/well in 200 $\mu$L of growth media.
4. Grow cells at least one day at 37° C., 5% $CO_2$.
5. Wash cells with D-PBS 1×.
6. Add 200 $\mu$L/well of starvation media (DMEM, 2.0 mM 1-Glutamine, 0.1% FBS). Incubate overnight at 37° C., 5% $CO_2$.
7. Dilute Compounds 1:20 in polypropylene 96 well plates using starvation media. Dilute dimethylsulfoxide 1:20 for use in control wells.
8. Remove starvation media from 96 well cell culture plates and add 162 $\mu$L of fresh starvation media to each well.
9. Add 18 $\mu$L of 1:20 diluted Compound dilution (from step 7) to each well plus the 1:20 dimethylsulfoxide dilution to the control wells (+/−VEGF), for a final dilution of 1:200 after cell stimulation. Final dimethylsulfoxide is 0.5%. Incubate the plate at 37° C., 5% $CO_2$ for two hours.
10. Remove unbound antibody from ELISA plates by inverting plate to remove liquid. Wash 3 times with TBSW+ 0.5% ethanolamine, pH 7.0. Pat the plate on a paper towel to remove excess liquid and bubbles.
11. Block plates with TBSW+0.5% Ethanolamine, pH 7.0, 150 $\mu$L per well. Incubate plate thirty minutes while shaking on a microliter plate shaker.
12. Wash plate 3 times as described in step 10.
13. Add 0.5 $\mu$g/well affinity purified anti-FLU-1 polyclonal rabbit antiserum. Bring final volume to 150 $\mu$L/well with TBSW+0.5% ethanolamine pH 7.0. Incubate plate for thirty minutes while shaking.
14. Add 180 $\mu$L starvation medium to the cells and stimulate cells with 20 $\mu$L/well 10.0 mM sodium ortho vanadate and 500 ng/mL VEGF (resulting in a final concentration of 1.0 mM sodium ortho vanadate and 50 ng/mL VEGF per well) for eight minutes at 37° C., 5% $CO_2$. Negative control wells receive only starvation medium.
15. After eight minutes, media should be removed from the cells and washed one time with 200 $\mu$L/well PBS.
16. Lyse cells in 150 $\mu$L/well HNTG while shaking at room temperature for five minutes. HNTG formulation includes sodium ortho vanadate, sodium pyro phosphate and EDTA.
17. Wash ELISA plate three times as described in step 10.
18. Transfer cell lysates from the cell plate to ELISA plate and incubate while shaking for two hours. To transfer cell lysate pipette up and down while scrapping the wells.
19. Wash plate three times as described in step 10.
20. Incubate ELISA plate with 0.02 $\mu$g/well UB40 in TBSW+05% ethanolamine. Bring final volume to 150 $\mu$L/well. Incubate while shaking for 30 minutes.
21. Wash plate three times as described in step 10.
22. Incubate ELISA plate with 1:10,000 diluted EIA grade goat anti-mouse IgG conjugated horseradish peroxidase in TBSW+0.5% ethanolamine, pH 7.0. Bring final volume to 150 $\mu$L/well. Incubate while shaking for thirty minutes.
23. Wash plate as described in step 10.
24. Add 100 $\mu$L of $ABTS/H_2O_2$ solution to well. Incubate ten minutes while shaking.
25. Add 100 $\mu$L of 0.2 M HCl for 0.1 M HCl final to stop the color development reaction. Shake 1 minute at room temperature. Remove bubbles with slow stream of air and read the ELISA plate in an ELISA plate reader at 410 nm.

The $IC_{50}$ values were measured for several of the compounds of the invention. These values are shown in Table 5.

TABLE 5

| Compound | $IC_{50}$ ($\mu$M) (% of inhibition at 100 $\mu$M) |
|---|---|
| IN-001 | +10.7% |
| IN-002 | +8.7% |
| IN-003 | +11% |
| IN-004 | +7% |
| IN-005 | 4.2 |
| IN-006 | +10.4% |
| IN-007 | +30% |
| IN-008 | +23% |
| IN-009 | 1.53 |
| IN-010 | 2.1 |
| IN-011 | +6.1% |
| IN-012 | +17.6% |
| IN-013 | +17% |
| IN-014 | +10% |
| IN-015 | +26% |
| IN-016 | +26% |
| IN-017 | +20.4% |
| IN-018 | +15.8 |
| IN-019 | +10.7 |
| IN-020 | >100 |
|  | 20.3 |

Example 3

Assay Measuring the Kinase Activity of the PDGF Receptor

All cell culture media, glutanine, and fetal bovine serum are purchased from Gibco Life Technologies (Grand Island, N.Y.) unless otherwise specified. All cells are grown in a humid atmosphere of 90–95% air and 5–10% $CO_2$ at 37° C. All cell lines are routinely subcultured twice a week and are negative for mycoplasma as determined by the Mycotect method (Gibco).

For ELISA assays, cells (U1242, obtained from Joseph Schlessinger, NYU) are grown to 80–90% confluency in growth medium (MEM with 10% FBS, NEAA, 1 mM NaPyr and 2 mM GLN) and seeded in 96-well tissue culture plates in 0.5% serum at 25,000 to 30,000 cells per well. After overnight incubation in 0.5% serum-containing medium cells are changed to serum-free medium and treated with test compound for 2 hr in a 5% $CO_2$, 37° C. incubator. Cells are then stimulated with ligand for 5–10 minute followed by lysis with HNTG (20 mM Hepes, 150 mM NaCl, 10% glycerol, 5 mM EDTA, 5 mM $Na_3VO_4$, 0.2% Triton X-100, and 2 mM NaPyr). Cell lysates (0.5 mg/well in PBS) are transferred to ELISA plates previously coated with receptor-specific antibody and which have been blocked with 5% milk in TBST (50 mM Tris-HCl pH 7.2, 150 mM NaCl and 0.1% Triton X-100) at room temperature for 30 min. Lysates are incubated with shaking for 1 hour at room temperature. The plates are washed with TBST four times and then incubated with polyclonal anti-phosphotyrosine antibody at room temperature for 30 minutes. Excess anti-phosphotyrosine antibody is removed by rinsing the plate with TBST four times. Goat anti-rabbit IgG antibody is added to the ELISA plate for 30 min at room temperature followed by rinsing with TBST four more times. ABTS (100 mM citric acid, 250 mM $Na_2HPO_4$ and 0.5 mg/mL 2,2'-azino-bis(3-ethybenzthiazoline-6-sulfonic acid)) plus $H_2O_2$ (1.2 mL 30% $H_2O_2$ to 10 mL ABTS) is added to the ELISA plates to start color development. Absorbance at 410 nm with a reference wavelength of 630 nm is recorded about 15 to 30 min after ABTS addition. The $IC_{50}$ values can be measured for the compounds of the invention.

Example 4

Assay Measuring the Kinase Activity of the FGF Receptor

The following protocol describes the reagents and procedures used to analyze protein tyrosine kinase activity of the Myc-GyrB-FGFR fusion protein.

Materials And Reagents
1. HNTG

| HEPES buffer pH 7.5 | 20 mM |
| --- | --- |
| NaCl | 150 mM |
| Triton X-100 | 0.2% |
| Glycerol | 10% |
| Aprotenin | 0.5 mg/mL |
| PMSF | 1 mM |

2. Kinase Buffer

| HEPES pH 7.2 | 50 mM |
| --- | --- |
| $MnCl_2$ | 10 mM |
| Triton-X-100 | 0.1% |
| DTT | 1.0 mM |

3. PBS (Phosphate Buffered Saline)

| KCL | 2.7 mM |
| --- | --- |
| $KH_2PO_4$ | 1.1 mM |
| $MgCl_2$(anhydrous) | 0.5 mM |
| NaCl | 138 mM |
| $Na_2HPO_4$ | 8.1 mM |

4. Blocking Buffer: TBB (Terene's Blocking Buffer)

| Tris pH 7.0–7.2 | 10 mM |
| --- | --- |
| NaCl | 100 mM |
| Tween-20 | 0.1% |
| BSA | 1.0% |

Note: One can make up this solution as a 10x stock, provided that it is sterile, filtered, and kept at 4° C.

5. PMSF Sigma Catalog #P-7626
   Make up as a 100 mM stock solution in 100% Ethanol
6. ATP (Bacterial source): Sigma Catalog #A-7699
   Make up as a 10 M stock adiquot and store in –20° C.
7. Biotin conjugated anti-phosphotyrosine mab: Upstate Biotechnology Inc. (Clone 4G10 cat. #16-103 ser. # 14495)
8. Voctastain Elite ABC reagent (Avidin peroxidase conjugate). Vector Laboratories (PK-6100).
9. ABTS (2.2'-azino-bist 3-ethylbeazthiazoline-6-sulfonic acid) Sigma CatalogA-1888

| Citric Acid | 100 mM |
| --- | --- |
| $Na_2HPO_4$ | 250 mM |
| pH to 4.0 with phosphoric acid | |
| ABTS | 0.5 mg/mL |

10. Hydrogen peroxide 30% solution: Fisher Catalog #H325.
    Store in the dark at 4° C. until ready to use.
11. ABTS/$H_2O_3$
    15 mL ABTS solution (above)
    2 μL $H_2O_2$
Prepare 5 minutes before use and leave at room temperature.
12. 0.2 M HCl
13. TRIS HCl: Fischer Catalog #BP 152-5
14. NaCl: Fischer Catalog #S271-10
15. HEPES: Fischer Catalog #BP310-500
16. TBST Buffer (Tris buffered Saline with Triton X-100)

| Tris pH 7.2 | 50 mM |
| --- | --- |
| NaCl | 150 mM |
| Triton X-100 | 0.1% |

17. DTT (Dichiothreitol) Fischer Catalog #BP172-25
    Make up as a 1 M stock aliquot and store in –20° C. Use once then discard remainder
18. $MnCl_2$: Manganese Chloride
    Make up as a 1 M stock.
19. Triton X-100
20. Affinity purified Rabbit αGST GyrB.
21. Corning 96-well ELISA plates (Corning cat. #25805-96)
22. DMSO (Dimethylsulfoxide): Sigma cat. # D-8418
23. Nune Polypropylene 96-well V bottom plates.

Procedure

All of the following steps are conducted at room temperature unless it is specifically indicated. All ELISA plate washing is by rinsing 4× with TBST.

1. Coat Corning 96 well ELISA plates with 1.0 μg/well of Rabbit αGyrB antibody in PBS for a total well volume of 100 μL. Store overnight at 4° C.
2. Remove unbound Rabbit antibody by inverting plate to remove liquid. Pat plate on a paper towel to remove excess liquid and bubbles
3. Add 100 μL of Blocking Buffer (TBB) to each well. Incubate while shaking on a microliter plate shaker at room temperature for 30 min.
4. Wash 4× with TBST. Pat plate on a paper towel to remove excess liquid and bubbles.
5. Add 15 μg COS/FGFR cell lysate Myc-GyrB-FGFR sources per well in HNTG for a final volume of 100 μL per well. Incubate while shaking on a micro-liter plate shaker at room temperature for 2 hours.
6. Wash 4× with TBST as described in step 4.
7. Add 80 μL of 1×kinase buffer per well.
8. Dilute compunds/extracts 1:10 (or as stated otherwise) in 1×kinase buffer+1% DMSO in a polypropylene 96 well plate.
9. At this point diluted Compounds/Extracts are added to the ELISA plate. Transfer 10 μL of diluted test and control wells from the polypropylene plate wells to the corresponding ELISA plate wells. Incubate while shaking on a micro-liter plate shaker at room temperature for 20 minutes.
10. Add 10 μL of 70 μM ATP diluted in kinase buffer to positive control and test wells (Final ATP concentration is 7 μM/well.) Add 10 μL of 1×kinase buffer to negative control wells. Incubate while shaking on a micro-liter plate shaker at room temperature for 15 min.
11. It is also critical to change pipette tips between each ATP addition. This will eliminate any chance of samples being carried over to other wells.
12. Stop Kinase reaction with the addition of 5 μL of 0.5 M EDTA pH 8.0 to all wells.
13. Wash 4× with TBST as described in step 4.
14. Add 100 μL per well of biotin conjugated α-phosphotyrosine mab (b-4G10) diluted in TBST. Incubate while shaking on a micro-liter plate shaker 30 minutes at room temperature while shaking.
15. Make up Vectastain ABC reagent. This step requires 30 min. for complete coupling of the avidin with the biotinylated HRP. Add on drop reagent A to 15 mL TBST. Mix by inverting tube several times. Then add one drop reagent B and mix again. Allow ABC reagent to mix at room temperature while the biotin-4G10 anti-phosphotyrosine is incubating in the assay plate.
16. Wash 4× with TBST as described in step 4.
17. Add 100 μL per well of ABC HRP reagent. Incubate while shaking on a micro-liter plate shaker at room temperature for 30 minutes.
18. Wash 4× with TBST and 1× with PBS.
19. Add 100 μL of ABTS/$H_2O_2$ solution to each well.
20. Incubate 5 to 15 minutes while shaking. Remove any bubbles.
21. If necessary stop reaction with the addition of 10 μL of 0.2 M HCl/well.
22. Read assay on Dynatech MR7000 ELISA Plate Reader. The $IC_{50}$ values can be measured for the compounds of the invention.

Example 5

Assay Measuring the Kinase Activity of the EGF Receptor

The following protocol describes the reagents and procedures used to analyze protein tyrosine kinase activity on the EGFR protein.

Materials and Reagents

1. Corning 96-well Elisa plate; Corning Catalog #25805-96
2. SUMO1 monoclonal anti-EGFR antibody
3. PBS (Phosphate Buffered Saline); Gibco Catalog #450-1300EB

| | |
|---|---|
| KCL | 2.7 mM |
| $KH_2PO_4$ | 1.1 mM |
| $MgCl_2$(anhydrous) | 0.5 mM |
| NaCl | 138 mM |
| $Na_2HPO_4$ | 8.1 mM |

4. TBST Buffer (Tris buffered Saline with Triton X-100)

| | |
|---|---|
| Tris pH 7.2 | 50 mM |
| NaCl | 150 mM |
| Triton X-100 | 0.1% |

5. Blocking Buffer

| | |
|---|---|
| Carnation Instant Milk 5% | 5.0 g/100 mL |
| PBS (as described above) | 100 mL |

6. A431 cell lysate
7. TBS Buffer

| | |
|---|---|
| Tris | 50 mM |
| NaCl | 150 mM |

8. TBS+10% DMSO

| | |
|---|---|
| Tris | 50 mM |
| NaCl | 150 mM |
| DMSO | 10% |

9. 1 mM ATP (ATP: Sigma Catalog #A-5394)
10. 1 M $MnCl_2$
11. ATP/$MnCl_2$ phosphorylation mix

| | |
|---|---|
| ATP 1 mM | 300 μL |
| $MnCl_2$ 1 M | 500 μL |

12. NUNC 96-well V bottom polypropylene plates (Applied Scientific Catalog #AS-72092)
13. EDTA 500 mM
14. Rabbit polyclonal anti-phosphotyrosine serum
15. Goat anti-rabbit IgG peroxidase conjugate (Biosource Catalog #ALI0404)
16. ABTS (2.2'-azino-bist 3-ethylbeazthiazoline-6-sulfonic acid) Sigma CatalogA-1888

| | |
|---|---|
| Citric Acid | 100 mM |
| $Na_2HPO_4$ | 250 mM |
| pH to 4.0 with phosphoric acid | |
| ABTS | 0.5 mg/mL |

17. Hydrogen peroxide 30% solution: Fisher Catalog # H325.
    Store in the dark at 4° C. until ready to use.
18. ABTS/$H_2O_3$
    15 mL ABTS solution (above)
    2 μL $H_2O_2$
    Prepare 5 minutes before use and leave at room temperature.
19. 0.2 M HCl Procedure All of the following steps are conducted at room temperature unless it is specifically indicated. All ELISA plate washing is by rinsing 4× with TBST.

1. Coat Corning 96 well ELISA plates with 0.5 μ/well of SUMO1 in a volume of 100 μL PBS. Store overnight at 4° C.
2. Remove unbound SUMO1 by inverting plate to remove liquid. Wash plates with distilled water. Pat plate on a paper towel to remove excess liquid and bubbles
3. Add 150 μL of Blocking Buffer to each well. Incubate while shaking on a microliter plate shaker at room temperature for 30 min.
4. Wash 3× with deionized water, then once with TBST. Pat plate on a paper towel to remove excess liquid and bubbles.
5. Dilute lysate in PBS (7 μg of lysate/100 μL of PBS).
6. Add 100 μL of diluted lysate to each well. Shake at room temperature for 60 min.
7. Wash as described in step 4.
8. Add 120 μL TBS to ELISA plate containing captured EGFR.
9. Dilute drugs/extracts 1:10 (unless specified otherwise) in TBS in 96-well polypropylene plates.
10. Add 13.5 μL diluted drugs/extracts to ELISA plate. To control wells (wells which do not receive any drug) add 13.5 μL of TBS+10% DMSO.
11. Incubate for 30 minutes while shaking at room temperature.
12. Add 15 μL phosphorylation mix directly to all wells except negative control well which does not receive ATP/$MnCl_2$. Incubate while shaking on a micro-liter plate shaker at room temperature for 5 min.
13. Stop Kinase reaction with the addition of 16.5 μL of 200 mM EDTA pH 8.0 to all wells.
14. Wash 4× with deionized water and twice with TBST.
15. Add 100 μL per well of anti-phosphotyrosine (1:3000 dilution in TBST). Incubate while shaking on a micro-liter plate shaker 30–45 minutes at room temperature while shaking.
16. Wash as described in step 4.
17. Add 100 μL per well of biosource Goat anti-rabbit IgG peroxidase conjugate (1:2000 dilution in TBST). Incubate 30 min. at room temperature while shaking.
18. Wash as described in step 4.
19. Add 100 μL of ABTS/$H_2O_2$ solution to each well.
20. Incubate 5 to 15 minutes while shaking. Remove any bubbles.
21. If necessary stop reaction with the addition of 10 μL of 0.2 M HCl/well.
22. Read assay on Dynatech MR7000 ELISA Plate Reader.

The $IC_{50}$ values were measured for several of the compounds of the invention. These values are shown in Table 8.

TABLE 8

| Compound | $IC_{50}$ (μM) |
|---|---|
| IN-001 | >100 |
| IN-002 | >100 |
| IN-003 | >100 |
| IN-004 | >100 |
| IN-005 | 8.2 |
| IN-006 | 30.8 |
|  | >100 |
| IN-007 | >100 |
| IN-008 | >100 |
| IN-009 | >100 |
| IN-010 | >100 |
| IN-011 | >100 |
| IN-012 | >100 |
| IN-013 | >100 |
| IN-014 | >100 |
| IN-015 | >100 |
| IN-016 | >100 |
| IN-017 | >100 |
| IN-018 | 17.8 |
|  | >100 |
| IN-019 | >100 |
| IN-020 | >100 |

Example 6

Assay Measuring the Activity of an Indolinone Compound Against VEGF and aFGF

The following protocol is used to measure a compound's activity against VEGF and aFGF, all of which are expressed by HUVEC cells.

Day 0

1. Wash and trypsinize HUV-EC—C cells (human umbilical vein endothelial cells, (American Type Culture Collection; catalogue no. 1730 CRL). Wash with Dulbecco's phosphate-buffered saline (D-PBS; obtained from Gibco BRL, catalogue no. 14190-029) 2 times at about 1 mL/10 $CM^2$ of tissue culture flask. Trypsinize with 0.05% trypsin-EDTA in non-enzymatic cell dissociation solution (Sigma Chemical Company; catalogue no. C-1544). The 0.05% trypsin was made by diluting 0.25% trypsin/1 mM EDTA (Gibco; catalogue no. 25200-049) in the cell dissociation solution. Trypsinize with about 1 mL/25–30 $cm^2$ of tissue culture flask for about 5 minutes at 37° C. After cells have detached from the flask, add an equal volume of assay medium and transfer to a 50 mL sterile centrifuge tube (Fisher Scientific; catalogue no. 05-539-6).

2. Wash the cells with about 35 niL assay medium in the 50 mL sterile centrifuge tube by adding the assay medium, centrifuge for 10 minutes at approximately 200×g, aspirate the supernatant, and resuspend with 35 mL D-PBS. Repeat the wash two more times with D-PBS, resuspend the cells in about 1 mL assay medium/15 $cm^2$ of tissue culture flask. Assay medium consists of F12K medium (Gibco BRL; catalogue no. 21127-014)+0.5% heat-inactivated fetal bovine serum. Count the cells with a Coulter Counter® (Coulter Electronics, Inc.) and add assay medium to the cells to obtain a concentration of 0.8–1.0×$10^5$ cells/mL.

3. Add cells to 96-well flat-bottom plates at 100 μL/well or 0.8–1.0×$10^4$ cells/well; incubate ~24 h at 37° C., 5% $CO_2$.

Day 1

1. Make up two-fold drug titrations in separate 96-well plates, generally 50 μM on down to 0 μM. Use the same assay medium as mentioned in day 0, step 2 above. Titrations are made by adding 90 μL/well of drug at 200 μM (4× the final well concentration) to the top well of a particular plate column. Since the stock drug concentration is usually 20 mM in DMSO, the 200 μM drug concentration contains 2% DMSO.

Therefore, diluent made up to 2% DMSO in assay medium (F12K+0.5% fetal bovine serum) is used as diluent for the drug titrations in order to dilute the drug but keep the DMSO concentration constant. Add this diluent to the remaining wells in the column at 60 µL/well. Take 60 µL from the 120 µL of 200 µM drug dilution in the top well of the column and mix with the 60 µL in the second well of the column. Take 60 µL from this well and mix with the 60 µL in the third well of the column, and so on until two-fold titrations are completed. When the next-to-the-last well is mixed, take 60 µL of the 120 µL in this well and discard it. Leave the last well with 60 µL of DMSO/media diluent as a non-drug-containing control. Make 9 columns of titrated drug, enough for triplicate wells each for 1) VEGF (obtained from Pepro Tech Inc., catalogue no. 100-200, 2) endothelial cell growth factor (ECGF) (also known as acidic fibroblast growth factor, or aFGF) (obtained from Boehringer Mannheim Biochemica, catalogue no. 1439 600); or, 3) human PDGF B/B (1276-956, Boehringer Mannheim, Germany) and assay media control. ECGF comes as a preparation with sodium heparin.

2. Transfer 50 µL/well of the drug dilutions to the 96-well assay plates containing the $0.8–1.0\times10^4$ cells/100 µL/well of the HUV-EC—C cells from day 0 and incubate ~2 h at 37° C., 5% $CO_2$.

3. In triplicate, add 50 µL/well of 80 µg/mL VEGF, 20 ng/mL ECGF, or media control to each drug condition. As with the drugs, the growth factor concentrations are 4× the desired final concentration. Use the assay media from day 0 step 2 to make the concentrations of growth factors. Incubate approximately 24 hours at 37° C., 5% $CO_2$. Each well will have 50 µL drug dilution, 50 µL growth factor or media, and 100 µL cells, =200 µL/well total. Thus the 4× concentrations of drugs and growth factors become 1× once everything has been added to the wells.

Day 2

1. Add $^3$H-thymidine (Amersham; catalogue no. TRK-686) at 1 µCi/well (10 µL/well of 100 µCi/mL solution made up in RPMI media+10% heat-inactivated fetal bovine serum) and incubate ~24 h at 37° C., 5% $CO_2$. RPMI was obtained from Gibco BRL, catalogue no. 11875-051.

Day 3

1. Freeze plates overnight at 20° C.

Day 4

1. Thaw plates and harvest with a 96-well plate harvester (Tomtec Harvester 96®) onto filter mats (Wallac; catalogue no. 1205-401); read counts on a Wallac Betaplate™ liquid scintillation counter.

The $IC_{50}$ values can be measured for the compounds of the invention.

Example 7

PDGF-, FGF-, and EGF-Induced BrdU Incorporation Assay

Materials and Reagents (1) PDGF: human PDGF B/B; 1276-956, Boehringer Mannheim, Germany (2) BrdU Labeling Reagent: 10 mM, in PBS (pH7.4), Cat. No. 1 647 229, Boehringer Mannheim, Germany.

(3) FixDenat: fixation solution (ready to use), Cat. No. 1 647 229, Boehringer Mannheim, Germany.

(4) Anti-BrdU-POD: mouse monoclonal antibody conjugated with peroxidase, Cat. No. 1 647 229, Boehringer Mannheim, Germany.

(5) TMB Substrate Solution: tetramethylbenzidine (TME), ready to use, Cat. No. 1 647 229, Boehringer Mannheim, Germany.

(6) PBS Washing Solution: 1×PBS, pH 7.4, made in house.

(7) Albumin, Bovine (BSA): fraction V powder; A-8551, Sigma Chemical Co., USA.

(8) 3T3 cell line genetically engineered to express human PDGF-R.

Protocol

1. Cells are seeded at 8000 cells/well in DMEM, 10% CS, 2 mM Gln in a 96 well plate. Cells are incubated overnight at 37° C. in 5% $CO_2$.

2. After 24 hours, the cells are washed with PBS, and then are serum starved in serum free medium (0% CS DMEM with 0.1% BSA) for 24 hours.

3. On day 3, ligand (PDGF=3.8 nM, prepared in DMEM with 0.1% BSA) and test compounds are added to the cells simultaneously. The negative control wells receive serum free DMEM with 0.1% BSA only; the positive control cells receive the ligand (PDGF) but no test compound. Test compounds are prepared in serum free DMEM with ligand in a 96 well plate, and serially diluted for 7 test concentrations.

4. After 20 hours of ligand activation, diluted BrdU labeling reagent (1:100 in DMEM, 0.1% BSA) is added and the cells are incubated with BrdU (final concentration=10 µM) for 1.5 hours.

5. After incubation with labeling reagent, the medium is removed by decanting and tapping the inverted plate on a paper towel. FixDenat solution is added (50 µL/well) and the plates are incubated at room temperature for 45 minutes on a plate shaker.

6. The FixDenat solution is thoroughly removed by decanting and tapping the inverted plate on a paper towel. Milk is added (5% dehydrated milk in PBS, 200 µL/well) as a blocking solution and the plate is incubated for 30 minutes at room temperature on a plate shaker.

7. The blocking solution is removed by decanting and the wells are washed once with PBS. Anti-BrdU-POD solution (1:100 dilution in PBS, 1% BSA) is added (100 µL/well), and the plate is incubated for 90 minutes at room temperature on a plate shaker.

8. The antibody conjugate is thoroughly removed by decanting and rinsing the wells 5 times with PBS, and the space is dried by inverting and tapping on a paper towel.

9. TMB substrate solution is added (100 µL/well) and incubated for 20 minutes at room temperature on a plate shaker until color development is sufficient for photometric detection.

10. The absorbance of the samples are measured at 410 nm (in "dual wavelength" mode with a filter reading at 490 nm, as a reference wavelength) on a Dynatech ELISA plate reader.

The $IC_{50}$ values can be measured for the compounds of the invention.

Example 8

Assay Measuring SRC Protein Kinase Activity

This assay is used to determine src protein kinase activity measuring phosphorylation of a biotinylated peptide as the readout.

1. Materials and Reagents a. Yeast transformed with src.

b. Cell lysates: Yeast cells expressing src are pelleted, washed once with water, re-pelleted and stored at −80° C. until use.

c. N-terminus biotinylated EEEYEEYEEEYEEEYEEEY is prepared by standard procedures well known to those skilled in the art.

d. DMSO: Sigma, St. Louis, Mo.
e. 96 Well ELISA Plate: Corning 96 Well Easy Wash, Modified flat Bottom Plate, Corning Cat. #25805-96.
f. NUNC 96-well V-bottom polypropylene plates for dilution of compounds: Applied Scientific Cat. #A-72092.
g. Vecastain ELITE ABC reagent: Vector, Burlingame, Calif.
h. Anti-src (327) mab: Schizosaccharomyces Pombe was used to express recombinant Src (Superti-Furga, et al., *EMBO J.*, 12:2625–2634; Superti-Furga, et al., *Nature Biochem.*, 14:600–605). S. Pombe strain SP200 (h-s leu1.32 ura4 ade21O) was grown as described and transformations were pRSP expression plasmids were done by the lithium acetate method (Superti-Furga, supra). Cells were grown in the presence of 1 $\mu$M thiamine to repress expression from the nmtl promoter or in the absence of thiamine to induce expression.
i. Monoclonal anti-phosphotyrosine, UBI 05-321 (UB40 may be used instead).
j. Turbo TMB-ELISA peroxidase substrate: Pierce Chemical.

2. Buffer Solutions
a. PBS (Dulbecco's Phosphate-Buffered Saline): GIBCO PBS, GIBCO Cat. #450-1300EB.
b. Blocking Buffer: 5% Non-fat milk (Carnation) in PBS.
c. Carbonate Buffer: $Na_2CO_4$ from Fischer, Cat. #S495, make up 100 mM stock solution.
d. Kinase Buffer: 1.0 mL (from 1 M stock solution) $MgCl_2$; 0.2 mL (from a 1 M stock solution) $MnCl_2$; 0.2 mL (from a 1 M stock solution) DTT; 5.0 mL (from a 1 M stock solution) HEPES; 0.1 mL TX-100; bring to 10 mL total volume with MilliQ $H_2O$.
e. Lysis Buffer: 5.0 HEPES (from 1 M stock solution.); 2.74 mL NaCl (from 5 M stock solution); 10 mL glycerol; 1.0 mL TX-100; 0.4 mL EDTA (from a 100 mM stock solution); 1.0 mL PMSF (from a 100 mM stock solution); 0.1 mL $Na_3VO_4$ from a 0.1 M stock solution); bring 100 mL total volume with MilliQ $H_2O$.
f. ATP: Sigma Cat. #A-7699, make up 10 mM stock solution (5.51 mg/mL).
g. TRIS-HCl: Fischer Cat. #BP 152-5, to 600 mL MilliQ $H_2O$ add 121.14 g material, adjust pH to 7.5 with HCl, bring to 1 L total volume with MilliQ $H_2O$.
h. NaCl: Fischer Cat. #S271-10, Make up 5 M stock solution with MilliQ $H_2O$.
i. $Na_3VO_4$: Fischer Cat. #S454-50; to 80 mL MilliQ $H_2O$, add 1.8 g material; adjust pH to 10.0 with HCl or NaOH; boil in a microwave; cool; check pH, repeat pH adjustment until pH readjustment stable after heating/cooling cycle; bring to 100 mL total volume with MilliQ $H_2O$; make 1 mL aliquots and store at 80° C.
j. $MgCl_2$: Fischer Cat. #M33-500, make up 1 M stock solution with MilliQ $H_2O$.
k. HEPES: Fischer Cat. #BP 310-500, too 200 mL MilliQ $H_2O$, add 59.6 g material, adjust pH to 7.5, bring to 250 mL total volume with MilliQ $H_2O$, sterile filter (1 M stock solution).
l. TBST Buffer: TBST Buffer: To 900 mL $dH_2O$ add 6.057 g TRIS and 8.766 g NaCl; adjust pH to 7.2 with HCl, add 1.0 mL Triton-$X_{100}$; bring to 1 L total volume with $dH_2O$.
m. MnCl2: Fischer Cat. #M87-100, make up 1 M stock solution with MilliQ $H_2O$.
n. DTT; Fischer Cat. #'BP172-5.
o. TBS (TRIS suffered Saline): to 900 mL MilliQ $H_2O$ add 6.057 g TRIS and 8.777 g NaCl; bring to 1 L total volume with MilliQ $H_2O$.
p. Kinase Reaction Mixture: Amount per assay plate (100 wells): 1.0 mL Kinase Buffer, 200 $\mu$g GST-$\zeta$, bring to final volume of 8.0 mL with MilliQ $H_2O$.
q. Biotin labeled EEEYEEYEEEYEEEYEEEY: Make peptide stock solution (1 mM, 2.98 mg/mL) in water fresh just before use.
r. Vectastain ELITE ABC reagent: To prepare 14 niL of working reagent, add 1 drop of reagent A to 15 mL TBST and invert tube several times to mix. Then add 1 drop of reagent B. Put tube on orbital shaker at room temperature and mix for 30 minutes.

3. Procedures
a. Preparation of src coated ELISA plate.
 1. Coat ELISA plate with 0.5 $\mu$g/well anti-src mab in 100 $\mu$L of pH 9.6 sodium carbonate buffer at 4° C. overnight.
 2. Wash wells once with PBS.
 3. Block plate with 0.15 mL 5% milk in PBS for 30 min. at room temperature.
 4. Wash plate 5× with PBS.
 5. Add 10 $\mu$g/well of src transformed yeast lysates diluted in Lysis Buffer (0.1 mL total volume per well). (Amount of lysate may vary between hatches.) Shake plate for 20 minutes at room temperature.
b. Preparation of phosphotyrosine antibody-coated ELISA plate.
 1. 4G10 plate: coat 0.5 $\mu$g/well 4G10 in 100 $\mu$L PBS overnight at 4° C. and block with 150 $\mu$L of 5% milk in PBS for 30 minutes at room temperature.
c. Kinase assay procedure.
 1. Remove unbound proteins from steps 1–7, above, and wash plates 5× with PBS.
 2. Add 0.08 mL Kinase Reaction Mixture per well (containing 10 $\mu$L of 10×Kinase Buffer and 10 $\mu$M (final concentration) biotin-EEEYEEYEEEYEEEYEEEY per well diluted in water.
 3. Add 10 $\mu$L of compound diluted in water containing 10% DMSO and pre-incubate for 15 minutes at room temperature.
 4. Start kinase reaction by adding 10 $\mu$L/well of 0.05 mM ATP in water (5 $\mu$M ATP final).
 5. Shake ELISA plate for 15 min. at room temperature.
 6. Stop kinase reaction by adding 10 $\mu$L of 0.5 M EDTA per well.
 7. Transfer 90 $\mu$L supernatant to a blocked 4G10 coated ELISA plate from section B, above.
 8. Incubate for 30 min. while shaking at room temperature.
 9. Wash plate 5× with TBST.
 10. Incubate with Vectastain ELITE ABC reagent (100 $\mu$L/well) for 30 min. at room temperature.
 11. Wash the wells 5× with TBST.
 12. Develop with Turbo TMB.

The $IC_{50}$ values were measured for several of the compounds of the invention. These values are shown in Table 8.

TABLE 8

| Compound | IC$_{50}$ ($\mu$M)<br>(% of inhibition at 100 $\mu$M) |
|---|---|
| IN-001 | −62% |
| IN-002 | −3.5% |
| IN-003 | >100 |
| IN-004 | −4.6% |
| IN-005 | 0.15 |
| IN-006 | >100 |
| IN-007 | +12.4% |
| IN-008 | −11% |
| IN-009 | 9 |
| IN-010 | 36.4% |
| IN-011 | −38.5% |
| IN-012 | −12% |
| IN-013 | −0.6% |
| IN-014 | −2.4% |
| IN-015 | +16% |
| IN-016 | +20.2% |
| IN-017 | +21.4% |
| IN-018 | +19.5% |
| IN-019 | −6.5% |
| IN-020 | +7.62% |

Example 9

Assay Measuring PYK-2 Protein Kinase Activity

This assay is used to determine pyk-2 protein kinase activity measuring phosphorylation of a biotinylated peptide as the readout.

1. Materials and Reagents
   a. Yeast transformed with pyk-2.
   b. Cell lysates: Yeast cells expressing pyk-2 are pelleted, washed once with water, re-pelleted and stored at −80° C. until use.
   c. N-terminus biotinylated EEEYEEYEEEYEEEYEEEY is prepared by standard procedures well known to those skilled in the art.
   d. DMSO: Sigma, St. Louis, Mo.
   e. 96 Well ELISA Plate: Corning 96 Well Easy Wash, Modified flat Bottom Plate, Corning Cat. #25805-96.
   f. NUNC 96-well V-bottom polypropylene plates for dilution of compounds: Applied Scientific Cat. #A-72092.
   g. Vecastain ELITE ABC reagent: Vector, Burlingame, Calif.
   h. Anti-pyk-2 mab: Schizosaccharomyces Pombe was used to express recombinant Pyk-2 (Superti-Furga, et al., EMBO J., 12:2625–2634; Superti-Furga, et al., Nature Biochem., 14:600–605). S. Pombe strain SP200 (h-s leul.32 ura4 ade21O) was grown as described and transformations were pRSP expression plasmids were done by the lithium acetate method (Superti-Furga, supra). Cells were grown in the presence of 1 $\mu$M thiamine to repress expression from the nmtl promoter or in the absence of thiamine to induce expression.
   i. Monoclonal anti-phosphotyrosine, UBI 05-321 (UB40 may be used instead).
   j. Turbo TMB-ELISA peroxidase substrate: Pierce Chemical.
2. Buffer Solution
   a. PBS (Dulbecco's Phosphate-Buffered Saline): GIBCO PBS, GIBCO Cat. #450-1300EB.
   b. Blocking Buffer: 5% Non-fat milk (Carnation) in PBS.
   c. Carbonate Buffer: Na$_2$CO$_4$ from Fischer, Cat. #S495, make up 100 mM stock solution.
   d. Kinase Buffer: 1.0 mL (from 1 M stock solution) MgCl$_2$; 0.2 mL (from a 1 M stock solution) MnCl$_2$; 0.2 mL (from a 1 M stock solution) DTT; 5.0 mL (from a 1 M stock solution) HEPES; 0.1 mL TX-100; bring to 10 mL total volume with MilliQ H$_2$O.
   e. Lysis Buffer: 5.0 HEPES (from 1 M stock solution.); 2.74 mL NaCl (from 5 M stock solution); 10 mL glycerol; 1.0 mL TX-100; 0.4 mL EDTA (from a 100 mM stock solution); 1.0 mL PMSF (from a 100 mM stock solution); 0.1 mL Na$_3$VO$_4$ from a 0.1 M stock solution); bring 100 mL total volume with MilliQ H$_2$O.
   f. ATP: Sigma Cat. #A-7699, make up 10 mM stock solution (5.51 mg/mL).
   g. TRIS-HCl: Fischer Cat. #BP 152-5, to 600 mL MilliQ H$_2$O add 121.14 g material, adjust pH to 7.5 with HCl, bring to 1 L total volume with MilliQ H$_2$O.
   h. NaCl: Fischer Cat. #S271-10, Make up 5 M stock solution with MilliQ H$_2$O.
   i. Na$_3$VO$_4$: Fischer Cat. #S454-50; to 80 mL MilliQ H20, add 1.8 g material; adjust pH to 10.0 with HCl or NaOH; boil in a microwave; cool; check pH, repeat pH adjustment until pH readjustment stable after heating/cooling cycle; bring to 100 mL total volume with MilliQ H$_2$O; make 1 mL aliquots and store at 80° C.
   j. MgCl$_2$: Fischer Cat. #M33-500, make up 1 M stock solution with MilliQ H$_2$O.
   k. HEPES: Fischer Cat. #BP 310-500, too 200 mL MilliQ H$_2$O, add 59.6 g material, adjust pH to 7.5, bring to 250 mL total volume with MilliQ H$_2$O, sterile filter (1 M stock solution).
   l. TBST Buffer: TBST Buffer: To 900 mL dH$_2$O add 6.057 g TRIS and 8.766 g NaCl; adjust pH to 7.2 with HCl, add 1.0 mL Triton-X100; bring to 1 L total volume with dH$_2$O.
   m. MnCl2: Fischer Cat. #M87-100, make up 1 M stock solution with MilliQ H$_2$O.
   n. DTT; Fischer Cat. #BP172-5.
   o. TBS (TRIS suffered Saline): to 900 mL MilliQ H$_2$O add 6.057 g TRIS and 8.777 g NaCl; bring to 1 L total volume with MilliQ H$_2$O.
   p. Kinase Reaction Mixture: Amount per assay plate (100 wells): 1.0 mL Kinase Buffer, 200 $\mu$g GST-ζ, bring to final volume of 8.0 mL with MilliQ H$_2$O.
   q. Biotin labeled EEEYEEYEEEYEEEYEEEY: Make peptide stock solution (1 mM, 2.98 mg/mL) in water fresh just before use.
   r. Vectastain ELITE ABC reagent: To prepare 14 mL of working reagent, add 1 drop of reagent A to 15 mL TBST and invert tube several times to mix. Then add 1 drop of reagent B. Put tube on orbital shaker at room temperature and mix for 30 minutes.
3. Procedures
   a. Preparation of pyk-2 coated ELISA plate.
      1. Coat ELISA plate with 0.5 $\mu$g/well anti-pyk-2 mab in 100 $\mu$L of pH 9.6 sodium carbonate buffer at 4° C. overnight.
      2. Wash wells once with PBS.
      3. Block plate with 0.15 mL 5% milk in PBS for 30 min. at room temperature.
      4. Wash plate 5x with PBS.
      5. Add 10 $\mu$g/well of pyk-2 transformed yeast lysates diluted in Lysis Buffer (0.1 mL total volume per well). (Amount of lysate may vary between hatches.) Shake plate for 20 minutes at room temperature.

b. Preparation of phosphotyrosine antibody-coated ELISA plate.
   1. 4G10 plate: coat 0.5 μg/well 4G10 in 100 μL PBS overnight at 4° C. and block with 150 μL of 5% milk in PBS for 30 minutes at room temperature.
c. Kinase assay procedure.
   1. Remove unbound proteins from steps 1–7, above, and wash plates 5× with PBS.
   2. Add 0.08 mL Kinase Reaction Mixture per well (containing 10 pL of 10×Kinase Buffer and 10 pM (final concentration) biotin-EEEYEEYEEEYEEEYEEEY per well diluted in water.
   3. Add 10 μL of compound diluted in water containing 10% DMSO and pre-incubate for 15 minutes at room temperature.
   4. Start kinase reaction by adding 10 μL/well of 0.05 mM ATP in water (5 μM ATP final).
   5. Shake ELISA plate for 15 min. at room temperature.
   6. Stop kinase reaction by adding 10 μL of 0.5 M EDTA per well.
   7. Transfer 90 μL supernatant to a blocked 4G10 coated ELISA plate from section B, above.
   8. Incubate for 30 min. while shaking at room temperature.
   9. Wash plate 5× with TBST.
   10. Incubate with Vectastain ELITE ABC reagent (100 μL/well) for 30 min. at room temperature.
   11. Wash the wells 5× with TBST.
   12. Develop with Turbo TMB.

The $IC_{50}$ values were measured for several of the compounds of the invention. These values are shown in Table 8.

TABLE 8

| Compound | $IC_{50}$ (μM) (% of inhibition at 100 μM) |
|---|---|
| IN-001 | −16% |
| IN-002 | +46.7% |
| IN-003 | +67.5% |
| IN-004 | +44.4% |
| IN-005 | 0.22 |
| IN-006 | +27% |
| IN-007 | +17.9% |
| IN-008 | 9.6 |
| IN-009 | 0.68 |
| IN-010 | 3.4 |
| IN-011 | +7.4% |
| IN-012 | +5.1% |
| IN-013 | −12% |
| IN-014 | −14% |
| IN-015 | +3.9% |
| IN-016 | −12.5% |
| IN-017 | −12% |
| IN-018 | +62% |
| IN-019 | −36% |
| IN-020 | +64.3% |

CONCLUSION

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims.

What is claimed is:

1. An indolinone compound having a structure set forth in formula I:

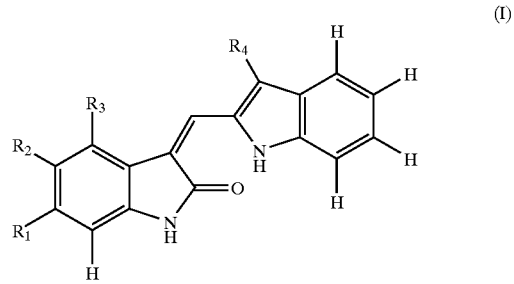

(I)

wherein
(a) $R_1$ is selected from the group consisting of hydrogen and halogen;
(b) $R_2$ is selected from the group consisting of
   (i) hydrogen;
   (ii) an amine of the formula —$(X_1)_{n1}$—$NX_2X_3$, or an imine of formula —$(X_1)$—$N=X_4$, wherein $X_1$ is sleeted from the group consisting of saturated or unsaturated alkyl and five-membered or six-membered aromatic, heteroaromatic, or aliphatic ring moieties and wherein n1 is 0, 1, or 2, and wherein $X_2$ and $X_3$ are independently selected from the group consisting of hydrogen, saturated or unsaturated alkyl, and five-membered or six-membered aromatic, heteroaromatic, or aliphatic ring moieties, or $X_2$ and $X_3$ taken together form a five-membered or six-membered heteroaliphatic or heteroaromatic ring, or wherein $X_4$ is an alkylene group optionally substituted with an aromatic or heteroaromatic monocyclic or bicyclic ring moiety;

(iii) a halogen;

(iv) a carboxylic acid of formula $-(X_6)_{n6}-COOH$ or an ester of the formula $-(X_7)_{n7}-COO-X_8$, wherein $X_6$, $X_7$, and $X_8$ are independently selected from the group consisting of alkyl and five-membered or six-membered aromatic, heteroaromatic, aliphatic, or heteroaliphatic ring moieties, and wherein n6 and n7 are each independently 0, 1, or 2;

(v) a sulfonamide of formula $-(X_{17})_{n17}-SO_2NX_{18}X_{19}$, wherein $X_{17}$ is selected from the group consisting of alkyl and five-membered or six-membered aromatic, heteroaromatic, aliphatic, or heteroaliphatic ring moieties optionally substituted with one or more substituents independently selected from the group consisting of alkyl, halogen, trihalomethyl, carboxylate, amino, nitro, or ester, and wherein n17 is 0, 1, or 2, and wherein $X_{18}$ and $X_{19}$ are each independently selected from the group consisting of alkyl and five-membered or six-membered aromatic, heteroaromatic, aliphatic, or heteroaliphatic ring moieties optionally substituted with one or more substituents independently selected form the group consisting of alkyl, halogen, trihalomethyl, carboxylate, amino, nitro, or ester, or wherein $X_{18}$ and $X_{19}$ taken together form a five-membered or six-membered aliphatic or heteroaliphatic ring optionally substituted with one or more substituents independently selected from the group consisting of alkyl, halogen, trihalomethyl, carboxylate, amino, nitro, or ester;

(vi) an aldehyde of formula $-(X_{20})_{n20}-C(O)H$ wherein $X_{20}$ is selected from the group consisting of saturated or unsaturated alkyl and five-membered or six-membered aromatic, heteroaromatic, aliphatic, or heteroaliphatic ring moieties, wherein said ring is optionally substituted with one or more substituents independently selected from the group consisting of alkyl, halogen, trihalomethyl, carboxylate, amino, nitro, or ester, and wherein n20 is 0, 1, or 2;

(vii) an amide of formula $-(X_{12})_{n12}-NHCOX_{13}$, or of formula $-(X_{14})_{n14}-CONX_{15}X_{16}$, wherein $X_{12}$ and $X_{14}$ are each independently selected from the group consisting of alkyl and five-membered or six-membered aromatic, heteroaromatic, aliphatic, or heteroaliphatic ring moieties, wherein said ring is optionally substituted with one or more substituents independently selected from the group consisting of alkyl, halogen, trihalomethyl, carboxylate, amino, nitro, or ester and wherein n12 and n14 are independently 0, 1, or 2, and wherein $X_{13}$, $X_{15}$ and $X_{16}$ are each independently selected from the group consisting of hydrogen, alkyl, hydroxyl and five-membered or six-membered aromatic, heteroaromatic, aliphatic, or heteroaliphatic ring moieties, wherein said ring is optionally substituted with one or more substituents independently selected from the group consisting of alkyl, halogen, trihalomethyl, carboxylate, amino, nitro, and ester; and (vii) a sulfone of formula $-(X_{21})_{n21}-SO_2-X_{22}$, wherein $X_{21}$ and $X_{22}$ are independently selected from the group consisting of saturated or unsaturated five-membered or six-membered aromatic, heteroaromatic, aliphatic, or heteroaliphatic ring moieties, wherein said ring is optionally substituted with one or more substituents independently selected from the group consisting of alkyl, halogen, trihalomethyl, carboxylate, amino, nitro, and ester, and wherein n21 is 0, 1, or 2; and (c) $R_3$ and $R_4$ are each independently selected from the group consisting of
   (i) hydrogen;
   (ii) saturated or unsaturated alkyl optionally substituted with substituents selected from the group consisting of halogen, trihalomethyl, carboxylate, amino, nitro, ester, and a five-membered or six-membered aromatic, heteroaromatic, aliphatic, or heteroaliphatic ring moiety, wherein said ring moiety is optionally substituted with one, two or three substituents independently selected from the group consisting of alkyl, halogen, trihalomethyl, carboxylate, amino, nitro and ester moieties;
   (iii) an aromatic or heteroaromatic ring optionally substituted with one, two, or three substitutuents independently selected from the group consisting of alkyl, alkoxy, halogen, trihalomethyl, carboxylate, amino, nitro, and ester moieties;
   (iv) an aliphatic or heteroaliphatic ring optionally substituted with one, two, or three substituents independently selected from the group consisting of alkyl, alkoxy, halogen, trihalomethyl, carboxylate, amino, nitro, ester, and an aromatic or heteroaromatic ring optionally substituted with one, two or three substituents independently selected from the group consisting of alkyl, alkoxy, halogen, trihalomethyl, carboxylate, amino, nitro and ester moieties;

with the proviso that the compound is not 3-(1H-indol-2-ylmethylene)-1,3-dihydro-indol-2-one.

2. The compound of claim 1, wherein
(a) $R_1$ is selected from the group consisting of hydrogen and halogen
(b) $R_2$ is selected from the group consisting of

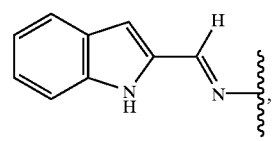

hydrogen, $-SO_2NXY$, $-COOH$, $-C(O)X$, NXY, and halogen, wherein X and Y are each independently selected from the group consisting of hydrogen and alkyl; and (c) $R_3$ and $R_4$ are each independently selected from the group consisting of hydrogen and alkyl.

3. The compound of claim 1, wherein
(a) $R_1$ is selected from the group consisting of hydrogen and chlorine;

(b) R₂ is selected from the group consisting of

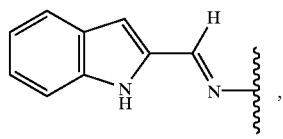

hydrogen, —SO₂NH₂, —COOH, —C(O)CH₃, NH₂, chlorine, and bromine; and (c) R₃ and R₄ are each independently selected from the group consisting of hydrogen and methyl.

4. An indolinone compound having the structure set forth in formula I:

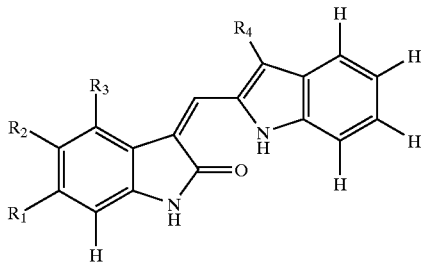

(I)

wherein (a) R₁ is selected from the group consisting of hydrogen and chlorine;

(b) R₂ is selected from the group consisting of

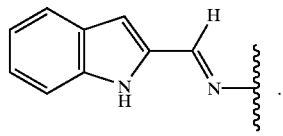

hydrogen, —SO₂NH₂, —COOH, —C(O)CH₃, NH₂, chlorine, and bromine; and (c) R₃ and R₄ are each independently selected from the group consisting of hydrogen and methyl; with the proviso that the compound is not 3-(1H-indol-2-ylmethylene)-1,3-dihydro-indol-2-one.

5. An indolinone compound selected from the group consisting of 5-methyl-3-(3-methyl-1H-indol-2-ymethylene)-1,3-dihydro-indol-2-one, 3-(3-methyl-1H-indol-2-ylmethylene)-2-oxo-2,3-dihydro-1H-indol-5-sulfonic acid amide, 3-(3-methyl-1H-indol-2-ylmethylene)-2-oxo-2,3-dihydro-1H-indole-5-sulfonic acid methylamide, 3-(3-methyl-1H-indole-2-ylmethylene)-2-oxo-2,3-dihydro-1H-indole-5-sulfonic acid dimethylamide, 3-(3-methyl-1H-indol-2-ylmethylene)-2-oxo-2,3-dihydro-1H-indole-5-carboxylic acid, 5-acetyl-3-(3-methyl-1H-indol-2-ylmethylene)-1,3-dihydro-indol-2-one, 5-acetyl-3-(1H-indol-2-ylmethylene)-1,3-dihydro-indol-2-one, 3-(1H-indol-2-ylmethylene)-2-oxo-2,3-dihydro-1H-indol-5-sulfonic acid amide, 5-amino-3-(1H-indol-2-ylmethylene)-1,3-dihydro-indol-2-one, 3-(1H-indol-2-ylmethylene)-2-oxo-2,3-dihydro-1H-indole-5-carboxylic acid, 6-chloro-3-(1H-indol-2-ylmethylene)-1,3-dihydro-indol-2-one, 5-chloro-3-(1H-indol-2-ylmethylene)-1,3-dihydro-indol-2-one, 5-bromo-3-(1H-indol-2-ylmethylene)-1,3-dihydro-indol-2-one, 3-(1H-indol-2-ylmethylene)-4-methyl-1,3-dihydro-indol-2-one, 3-(3-methyl-1H-indol-2-ylmethylene)-1,3-dihydro-indol-2-one, 5-chloro-3-(3-methyl-1H-indol-2-ylmethylene)-1,3-dihydro-indol-2-one, 5-bromo-3-(3-methyl-1H-indol-2-ylmethylene)-1,3-dihydro-indol-2-one, 4-methyl-3-(3-methyl-1H-indol-2-ylmethylene)-1,3-dihydro-indol-2-one, and 3-(1H-indol-2-ylmethylene)-5[(1H-indol-2-ylmethylene)-amino]-1,3-dihydro-indol-2-one.

6. A pharmaceutical composition comprising
  (i) a physiologically acceptable carrier, diluent, or excipient or a combination thereof; and
  (ii) a compound of claim 1.

7. A method of inhibiting the function of a protein tyrosine kinase in vitro with an indolinone compound of claim 1, comprising the steps of:
  (a) contacting cells expressing said protein tyrosine kinase with said compound; and
  (b) monitoring an effect upon said cells.

8. The method of claim 7, wherein said effect is selected from the group consisting of a change or absence of a change in cell phenotype, a change or absence of change in cell proliferation, a change or absence of a change in the catalytic activity of said protein tyrosine kinase, a change or absence of a change in the interaction between said protein tyrosine kinase and a natural binding partner, and measuring phosphate concentration.

9. The method of claim 7, comprising the following steps:
  (i) lysing said cells to render a lysate comprising tyrosine kinase;
  (ii) adsorbing said protein tyrosine kinase to an antibody;
  (iii) incubating said adsorbed protein tyrosine kinase with a substrate or substrates; and
  (iv) adsorbing said substrate or substrates to a solid support or antibody;
  wherein said step of monitoring said effect on said cells comprises measuring the phosphate concentration of said substrate or substrates.

10. A method for treating a disease related to unregulated tyrosine kinase signal transduction, the method comprising the step of administering to a subject in need thereof a therapeutically effective amount of a compound of claim 1.

11. The method of claim 10 wherein said disease is selected from the group consisting of hypertension, depression, generalized anxiety disorder, phobias, post-traumatic stress syndrome, avoidant personality disorder, sexual dysfunction, eating disorders, obesity, chemical dependencies, cluster headache, migraine, pain, Alzheimer's disease, obsessive-compulsive disorder, panic disorder, memory disorders, Parkinson's disease, endocrine disorders, vasospasm, cerebellar ataxia, and gastrointestinal tract disorders.

12. The method of claim 10, wherein the disease is cancer.

13. The method of claim 10, wherein said cancer is selected from the group consisting of glioblastoma, head, neck, lung, bladder, squamous cell, breast, ovarian, gastric, pancreas, prostate, melanoma, hepatocellular, colorectal, thyroid, leukemia and lymphoma.

* * * * *